(12) United States Patent
Ahmed et al.

(10) Patent No.: US 9,187,467 B2
(45) Date of Patent: Nov. 17, 2015

(54) 2-PHENYL BENZOTHIAZOLE LINKED IMIDAZOLE COMPOUNDS AS POTENTIAL ANTICANCER AGENTS AND PROCESS FOR THE PREPARATION THEREOF

(75) Inventors: Kamal Ahmed, Andhra Pradesh (IN); Ratna Reddy Challa, Andhra Pradesh (IN); Prabhakar Singaraboina, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 109 days.

(21) Appl. No.: 13/696,549

(22) PCT Filed: Feb. 15, 2012

(86) PCT No.: PCT/IB2012/050678
§ 371 (c)(1),
(2), (4) Date: Nov. 6, 2012

(87) PCT Pub. No.: WO2012/110959
PCT Pub. Date: Aug. 23, 2012

(65) Prior Publication Data
US 2015/0141657 A1    May 21, 2015

(51) Int. Cl.
*C07D 417/10* (2006.01)
*C07D 417/14* (2006.01)

(52) U.S. Cl.
CPC ............ *C07D 417/10* (2013.01); *C07D 417/14* (2013.01)

(58) Field of Classification Search
USPC .................................................. 548/152, 178
See application file for complete search history.

(56) References Cited

U.S. PATENT DOCUMENTS

2006/0063816 A1    3/2006  Stevens et al.

FOREIGN PATENT DOCUMENTS

WO    WO-2008/084218 A1 *  7/2008

OTHER PUBLICATIONS

International Search Report dated Jun. 12, 2012 for PCT application No. PCT/IB2012/050678.
Written Opinion dated Jun. 12, 2012 for PCT application No. PCT/IB2012/050678.
Mortimer et al; "Antitumor Benzothiazoles. 26. 2-(3,4-Dimethoxyphenyl)-5-fluorobenzothiazole (GW 610, NSC 721648), a Simple Fluorinated 2-Arylbenzothiazole, Shows Potent and Selective Inhibitory Activity against Lung, Colon, and Breast Cancer Cell Lines"; Journal of Medical Chemistry, 2006, vol. 49; pp. 179-185.
Hutchinson et al; "Antitumor Benzothiazoles. 14. Synthesis and in Vito Biological Properties of Fluorinated 2-(4-Aminophenyl) Benzothiazoles"; Journal of Medical Chemistry, Apr. 19, 2001, vol. 44; pp. 1446-1455.
Wang et al; "Potent, Orally Active Heterocycle-Based Combretastatin A-4 Analogues: Synthesis, Structure-Activity Relationship, Pharmacokientics, and in Vivo Antitumor Activity Evaluation"; Journal of Medical Chemistry, Mar. 13, 2002; pp. 1697-1711.
Simoni et al; "Novel Combretastatin Analogues Endowed with Antitumor Activity"; Journal of Medical Chemisty, May 6, 2006; pp. 3143-3152.
Ohsumi et al; "Syntheses and Antitumor Activity of Cis-Restricted Combretastatins: 5-Membered Heterocyclic Analogues"; Bioorganic & Medical Chemistry Letters 8, Sep. 25, 1998; pp. 3153-3158.
Shi et al; "Antitumor Benzothiazoles. 3. Synthesis of 2-(4-Aminophenyl) benzothiazoles and Evaluation of Their Activites against Breast Cancer Cell Lines in Vitro and in Vivo"; Journal of Medical Chemistry, Jul. 15, 1996; pp. 3375-3384.

* cited by examiner

*Primary Examiner* — Laura L. Stockton
(74) *Attorney, Agent, or Firm* — Ohlandt, Greeley, Ruggiero & Perle, LLP

(57)    ABSTRACT

The present invention provides 2-phenyl benzothiazole linked imidazole compounds of formula A as anti cancer agent against fifty three human cancer cell lines.

General formula A

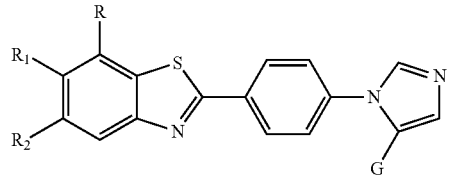

wherein

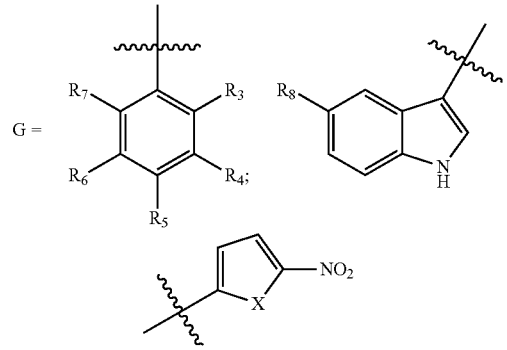

X = NH, S

R = H or $OCH_3$;
$R_1$ = H, F or $OCH_3$;
$R_2$ = H or $OCH_3$;
$R_3$ = H, $NH_2$, F or $OCH_3$;
$R_4$ = H, $NH_2$ or $OCH_3$;
$R_5$ = H, $NH_2$, F, $CF_3$ or $OCH_3$;
$R_6$ = H or $OCH_3$;
$R_7$ = H or $OCH_3$;
$R_8$ = H or $OCH_3$.

18 Claims, 3 Drawing Sheets

2-PHENYL BENZOTHIAZOLE LINKED IMIDAZOLE COMPOUNDS AS POTENTIAL ANTICANCER AGENTS AND PROCESS FOR THE PREPARATION THEREOF

FIELD OF THE INVENTION

The present invention relates to 2-phenyl benzothiazole linked imidazole compounds of general formula A as potential anticancer agents and a process for the preparation thereof General formula A wherein

G =

$R = H$ or $OCH_3$;
$R_1 = H$, F or $OCH_3$;
$R_2 = H$ or $OCH_3$;
$R_3 = H$, $NH_2$, F or $OCH_3$;
$R_4 = H$, $NH_2$ or $OCH_3$;
$R_5 = H$, $NH_2$, F, $CF_3$ or $OCH_3$;
$R_6 = H$ or $OCH_3$;
$R_7 = H$ or $OCH_3$;
$R_8 = H$ or $OCH_3$.

The structural formula of the representative group of 2-phenyl benzothiazole linked imidazole compounds are given below:

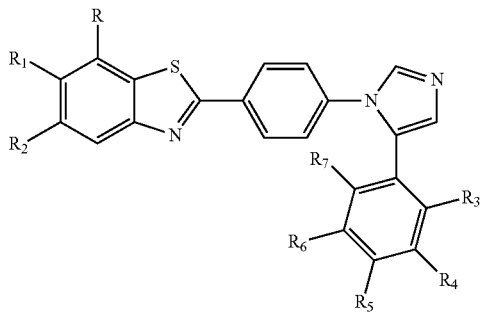

$R = H, OCH_3$
$R_1 = H, F, OCH_3$
$R_2 = H, OCH_3$
$R_3 = H, OCH_3, NH_2, F$
$R_4 = H, OCH_3, NH_2$ $R_5 = H, F, NH_2, CF_3, OCH_3,$
$R_6 = H, OCH_3$
$R_7 = H, OCH_3$
$R_8 = H, OCH_3$

Formula 4a-j to 7a-j

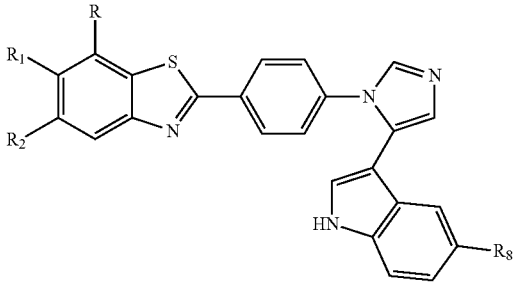

$R = H, OCH_3$
$R_1 = H, F, OCH_3$
$R_2 = H, OCH_3$
$R_8 = H, OCH_3$

Formula 8a-b to 11a-b

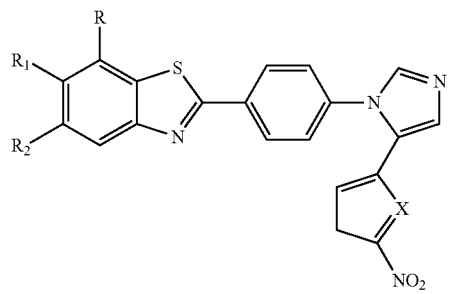

$R = H, OCH_3$
$R_1 = H, F, OCH_3$
$R_2 = H, OCH_3$
$X = O, S$

Formula 12a-b to 15a-b

BACKGROUND OF THE INVENTION

Microtubules are composed of dynamic polymers of tubulin which are involved in various cellular processes such as cell division and cell shape, especially in induction of apoptosis. Rapidly dividing cells are more susceptible to tubulin polymerization inhibitors than non-dividing cells and impair microtubule dynamics and consequently arrest cells during mitosis (Jordan, M. A.; Hadfield, J. A.; Lawrence, N. J.; McGown, A. T. *Med. Res. Rev.*, 1998, 18, 259-296). The mode of action of tubulin inhibitors is that they bind to the tubulin binding sites thereby stabilizing or destabilizing microtubule assembly. Disruption of microtubule leads to cell cycle arrest at G2/M phase followed by apoptotic cell death (Pasquier, E.; Kavallaris, M. *IUBMB Life*., 2008, 60, 165-170).

Combretastatins are a class of naturally occurring compounds isolated from the African willow tree combretum caffrum has shown considerable interest and shown to be potent tubulin inhibitor and attracted the medicinal chemists in the design of various combretastatins analogs (Pettit, G. R.; Singh, S. B.; Hamel, E.; Lin, C. M.; Alberts, D. S.; Garcia Kendall, D. *Experientia* 1989, 45, 209). Combretastatin A-4 (1) a simple cis stilbene has been reported to exhibit potent cytotoxicity against various cancer cell lines including multi drug resistant cells exhibiting excellent anticancer activity and found to be inhibit polymerization of tubulin by binding to the colchicine site. But CA-4 failed to show in vivo efficacy due to its poor water solubility and its pro drug of CA-4 disodium phosphate derivative (CA-4P) exhibiting promising results and presently in clinical trails (Buolamwini, J. K. *Curr. Opin. Chem. Biol*., 1999, 3, 500-509). The structure-activity relationship (SAR) information confirmed the importance of cis-stereochemistry and trimethoxy substituents in the A-ring and a new combretastatin derivatives with B-ring modifications by replacement of phenyl group with benzo[b] thiophene and benzofuran combretastatin analogues (ST2151) and (ST2179) and their phosphate prodrugs were synthesized and exhibiting high antitumor activity in both in vitro and in vivo models (Simoni, D.; Romagnoli, R.; Baruchello, R.; Rondanin, R.; Rizzi, M.; Pavani, M. G.; Alloatti, D.; Giannini, G.; Marcellini, M.; Riccioni, T.; Castorina, M.; Guglielmi, M. B.; Bucci, F.; Carminati, P.; Pisano, C. *J. Med. Chem*. 2006, 49, 3143-3152). Various series of compounds with heterocycles in place of the cis double bond in combretastatin A-4 (CA-4) furnished various novel heterocyclic CA-4 analogues. These compound showing anticancer activity and also antitubulin activity in a variety of tumor models while retaining the characteristics of CA-4. These compounds include where tetrazole ring could replace the cis double bond to maintain potent cytotoxicity. All these compounds showed excellent antitumor activities against the colon 26 murine tumors when given intravenously (Ohsumi, K.; Hatanaka, T.; Fujita, K.; Nakagawa, R.; Fukuda, Y.; Nihei, Y.; Suga, Y.; Morinaga, Y.; Akiyama, Y.; Tsuji, T. *Bioorg. Med. Chem. Lett*. 1998, 8, 3153). Moreover a novel series of compounds consisting of 1,2- and 1,5 substituted five-membered aromatic heterocycles such as imidazole, oxazole, and pyrazole to mimic the cis double bond in CA-4 were synthesized particularly based on 1,5 diphenylsubstituted imidazoles (2) these compounds exhibited significant anticancer activity compared to that CA-4 (Wang, L.; Woods, K. W.; Li, Q.' Barr, K. J.; McCroskey, R. W.; Hannick, S. M.; Gherke, L.; Credo, R. B.; Hui, Y. H.; Marsh, K.; Warner, R.; Lee, J. Y.; Zielinski-Mozng, N.; Frost, D.; Rosenberg, S. H.; Sham, H. L. *J. Med. Chem*. 2002, 45, 1697-1711).

Benzothiazoles are a class of compounds comprising various activities including anticancer activity wherein 2-(4-Aminophenyl) benzothiazoles (3) and 2-(4-hydroxyphenyl) benzothiazoles are novel class of potent and selective antitumor agents and found to exhibit antitumor activity particularly against certain breast carcinoma cell lines MCF-7, MDA 468 with $IC_{50}$<1 nM to be promising anticancer activity both in vitro and in vivo also (Shi, D. F.; Bradshaw, T. D.; Wrigley, S.; McCall, C. J.; Lelieveld, P.; Fichtner, I.; Stevens, M. F. *J. Med. Chem*. 1996, 39, 3375-3384). Various fluorinated and 2-(3,4-dimethoxyphenyl)-5-fluorobenzothiazole were reported to be anticancer agents and these compounds shown to exhibit potent and selective inhibitory activity against lung, colon, and breast cancer cell lines. (Hutchinson, A.; Chua, M.; Browne, H. L.; Trapani, V.; Bradshaw, T. D; Westwell, A. D; Stevens, M. F. *J. Med. Chem*. 2001, 44, 1446-1455" and "Mortimer, C. G.; Wells, G.; Crochard, J. P.; Stone, E. L.; Bradshaw, T. D.; Stevens, M. F.; Westwell, A. D. *J. Med. Chem*. 2006, 49, 179-185).

Keeping this aspect in mind, 2-phenyl benzothiazole linked imidazole compound were designed and synthesized comprising of 2-phenyl benzothiazoles and imidazole moiety by forming 1, 5 oriented 2-phenyl benzothiazole and various phenyl ring and also various heteroaromatic ring systems maintaining cis conformation which are expected to possess promising anticancer activity. Additionally, these are structurally simple small molecules.

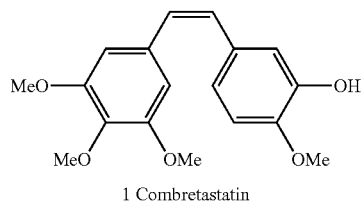

1 Combretastatin

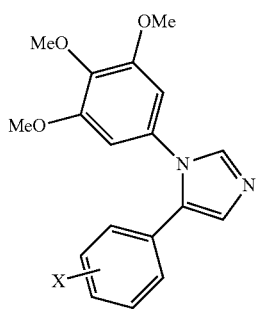

2 Imidazo Combretastatin

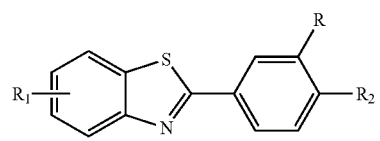

3a R = CH$_3$, R$_1$ = H; R$_2$ = NH$_2$
3b R = CH$_3$, R$_2$ = 6-OH R$_2$ = NH$_2$
3c R, R$_2$ = OMe, R$_1$ = 5-F
3d R, R$_2$ = OMe, R$_1$ = 6-F

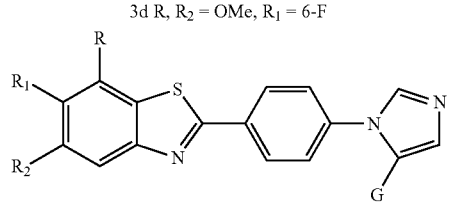

4-amino phenyl benzothiazoles 2-phenyl benzothiazole linked imidazoles (general formula 7)

References may be made to U.S. Pat. No. 7,384,966, wherein compound of formula X has been reported.

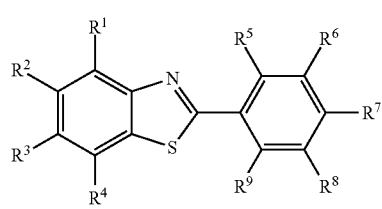

General formula X

The structures of patent proposal are different with the compounds of general formula X. In general formula X, $R_7$ is comprising of imidazole ring with different functional groups like hydroxy, hydroxy alkyl, acyl, acetamide, carboxyl, cyano, carboxamide, sulfonamide, sulfone, oxide, alkoxy and nitro. Where as in subject patent proposal, the structure is comprising of imidazole ring with aryl and heteroaryl ring systems which are present on position-5. These are not included in the cited U.S. Pat. No. 7,384,966 (shown in below figure).

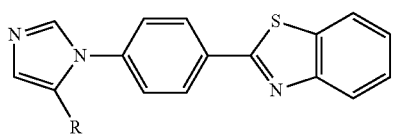

R = substituted aryl, heteroaryl

Structure of present propasal

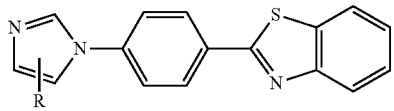

R = hydroxy, hydroxy alkyl, acyl, acetamide, carboxyl, cyano, carboxamide, sulfonamide, sulfone, oxide, alkoxy, nitro Structure of patent US 7384966

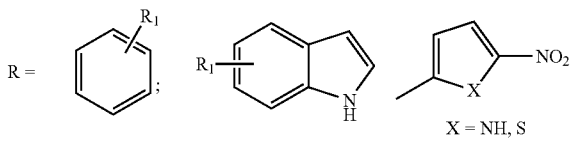

$R_1$ = different substitutions

OBJECTIVES OF THE INVENTION

The main objective of the present invention is to provide 2-phenyl benzothiazole linked imidazole compounds of general formula A useful as anticancer agent.

Another objective of the present invention is to provide process for the preparation of 2-phenyl benzothiazole linked imidazole compounds of general formula A.

SUMMARY OF THE INVENTION

Accordingly, present invention provides compounds of general formula A

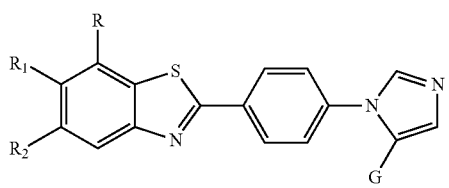

General formula A wherein

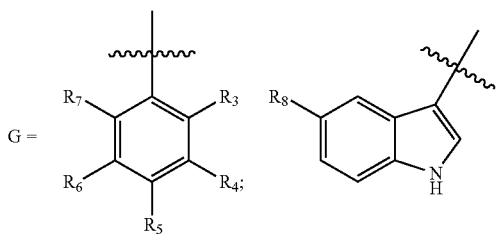

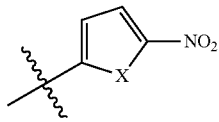

X = NH, S

R = H or $OCH_3$;
$R_1$ = H, F or $OCH_3$;
$R_2$ = H or $OCH_3$;
$R_3$ = H, $NH_2$, F or $OCH_3$;
$R_4$ = H, $NH_2$ or $OCH_3$;
$R_5$ = H, $NH_2$, F, $CF_3$ or $OCH_3$;
$R_6$ = H or $OCH_3$;
$R_7$ = H or $OCH_3$;
$R_8$ = H or $OCH_3$.

In an embodiment of the present invention, representative group of 2-phenyl benzothiazole linked imidazole compounds are:

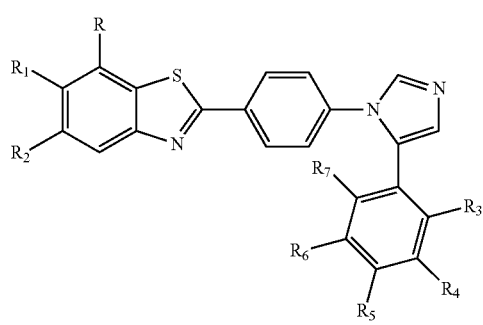

R = H, $OCH_3$         $R_5$ = H, F, $NH_2$, $CF_3$, $OCH_3$,
$R_1$ = H, F, $OCH_3$   $R_6$ = H, $OCH_3$
$R_2$ = H, $OCH_3$      $R_7$ = H, $OCH_3$
$R_3$ = H, $OCH_3$, $NH_2$, F   $R_8$ = H, $OCH_3$
$R_4$ = H, $OCH_3$, $NH_2$

Formula 4a-j to 7a-j

-continued

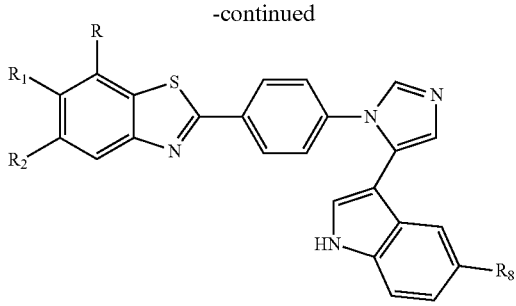

R = H, OCH₃
R₁ = H, F, OCH₃
R₂ = H, OCH₃
R₈ = H, OCH₃

Formula 8a-b to 11a-b

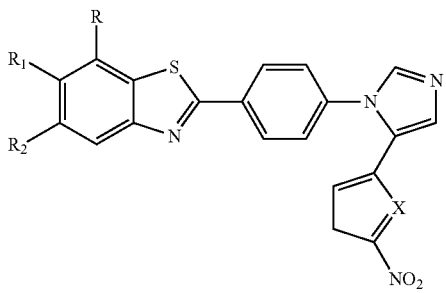

R = H, OCH₃
R₁ = H, F, OCH₃
R₂ = H, OCH₃
X = O, S

Formula 12a-b to 15a-b

In yet another embodiment of the present invention, representative compounds are:

6-Fluoro-2-(4-(5-phenyl-1H-imidazol-1-yl)phenyl)benzo[d]thiazole (4a);
6-Fluoro-2-(4-(5-(4-(trifluoromethyl)phenyl)-1H-imidazol-1yl)phenyl)benzo[d]thiazole (4b);
6-Fluoro-2-(4-(5-(4-fluoro-3-methoxyphenyl)-1H-imidazol-1-yl)phenyl)benzo[d]thiazole (4c);
2-(4-(5-(3,5-Dimethoxyphenyl)-1H-imidazol-1-yl)phenyl)-6-fluorobenzo[d]thiazole (4d);
2-(4-(5-(3,4-Dimethoxyphenyl)-1H-imidazol-1-yl)phenyl)-6-fluorobenzo[d]thiazole (4e);
6-Fluoro-2-(4-(5-(3,4,5-trimethoxyphenyl)-1H-imidazol-1-yl)phenyl)benzo[d]thiazole (4f);
6-Fluoro-2-(4-(5-(2,4,6-trimethoxyphenyl)-1H-imidazol-1-yl)phenyl)benzo[d]thiazole (4g);
4-(1-(4-(6-Fluorobenzo[d]thiazol-2-yl)phenyl)-1H-imidazol-5-yl)benzenamine (4h);
2-(1-(4-(6-Fluorobenzo[d]thiazol-2-yl)phenyl)-1H-imidazol-5-yl)-5-methoxybenzeneamine (4i)
5-(1-(4-(6-Fluorobenzo[d]thiazol-2-yl)phenyl)-1H-imidazol-5-yl)-2-methoxy benzenamine (4j);
6-Methoxy-2-(4-(5-phenyl-1H-imidazol-1-yl)phenyl)benzo[d]thiazole (5a);
6-Methoxy-2-(4-(5-(4-(trifluoromethyl)phenyl)-1H-imidazol-1-yl)phenyl)benzo[d]thiazole (5b);
2-(4-(5-(4-Fluoro-3-methoxyphenyl)-1H-imidazol-1-yl)phenyl)-6-methoxybenzo[d]thiazole (5c);
2-(4-(5-(3,5-Dimethoxyphenyl)-1H-imidazol-1-yl)phenyl)-6-methoxybenzo[d]thiazole (5d);
2-(4-(5-(3,4-Dimethoxyphenyl)-1H-imidazol-1-yl)phenyl)-6-methoxybenzo[d]thiazole (5e);
6-Methoxy-2-(4-(5-(3,4,5-trimethoxyphenyl)-1H-imidazol-1-yl)phenyl)benzo[d]thiazole (5f);
6-Methoxy-2-(4-(5-(2,4,6-trimethoxyphenyl)-1H-imidazol-1-yl)phenyl)benzo[d]thiazole (5g);
4-(1-(4-(6-Methoxybenzo[d]thiazol-2-Ophenyl)-1H-imidazol-5-yl)benzenamine (5h)
5-Methoxy-2-(1-(4-(6-methoxybenzo[d]thiazol-2-yl)phenyl)-1H-imidazol-5-yl)benzene amine (5i);
2-Methoxy-5-(1-(4-(6-methoxybenzo[d]thiazol-2-yl)phenyl)-1H-imidazol-5-yl)benzene amine (5j);
5,7-Dimethoxy-2-(4-(5-phenyl-1H-imidazol-1-yl)phenyl)benzo[d]thiazole (6a);
5,7-Dimethoxy-2-(4-(5-(4-(trifluoromethyl)phenyl)-1H-imidazol-1-yl)phenyl)benzo[d]thiazole (6b);
2-(4-(5-(4-Fluoro-3-methoxyphenyl)-1H-imidazol-1-yl)phenyl)-5,7-dimethoxybenzo[d]thiazole (6c)
2-(4-(5-(3,5-Dimethoxyphenyl)-1H-imidazol-1-yl)phenyl)-5,7-dimethoxybenzo[d]thiazole (6d);
2-(4-(5-(3,4-Dimethoxyphenyl)-1H-imidazol-1-yl)phenyl)-5,7-dimethoxybenzo[d]thiazole (6e);
5,7-Dimethoxy-2-(4-(5-(3,4,5-trimethoxyphenyl)-1H-imidazol-1-yl)phenyl)benzo[d]thiazole (6f);
5,7-Dimethoxy-2-(4-(5-(2,4,6-trimethoxyphenyl)-1H-imidazol-1-yl)phenyl)benzo[d]thiazole (6g);
4-(1-(4-(5,7-Dimethoxybenzo[d]thiazol-2-yl)phenyl)-1H-imidazol-5-yl)benzenamine (6h);
2-(1-(4-(5,7-Dimethoxybenzo[d]thiazol-2-yl)phenyl)-1H-imidazol-5-yl)-5-methoxybenzenamine (6i);
5-(1-(4-(5,7-Dimethoxybenzo[d]thiazol-2-yl)phenyl)-1H-imidazol-5-yl)-2-methoxy benzenamine (6j);
5,6,7-Trimethoxy-2-(4-(5-phenyl-1H-imidazol-1-yl)phenyl)benzo[d]thiazole (7a);
5,6,7-Trimethoxy-2-(4-(5-(4-(trifluoromethyl)phenyl)-1H-imidazol-1-yl)phenyl)benzo[d]thiazole (7b);
2-(4-(5-(4-Fluoro-3-methoxyphenyl)-1H-imidazol-1-yl)phenyl)-5,6,7-trimethoxybenzo[d]thiazole (7c);
2-(4-(5-(3,5-Dimethoxyphenyl)-1H-imidazol-1-yl)phenyl)-5,6,7-trimethoxybenzo[d]thiazole (7d);
2-(4-(5-(3,4-Dimethoxyphenyl)-1H-imidazol-1-yl)phenyl)-5,6,7-trimethoxybenzo[d]thiazole (7e);
5,6,7-Trimethoxy-2-(4-(5-(3,4,5-trimethoxyphenyl)-1H-imidazol-1-yl)phenyl)benzo[d]thiazole (7f);
5,6,7-Trimethoxy-2-(4-(5-(2,4,6-trimethoxyphenyl)-1H-imidazol-1-yl)phenyl)benzo[d]thiazole (7g);
4-(1-(4-(5,6,7-Trimethoxybenzo[d]thiazol-2-yl)phenyl)-1H-imidazol-5-yl)benzenamine (7h);
2-(1-(4-(5,7-Dimethoxybenzo[d]thiazol-2-yl)phenyl)-1H-imidazol-5-yl)-5-methoxy benzenamine (7i);
2-Methoxy-5-(1-(4-(5,6,7-trimethoxybenzo[d]thiazol-2-yl)phenyl)-1H-imidazol-5-yl)benzeneamine (7j);
2-(4-(5-(1H-Indol-3-yl)-1H-imidazol-1-yl)phenyl)-6-fluorobenzo[d]thiazole (8a);
6-Fluoro-2-(4-(5-(5-methoxy-1H-indol-3-yl)-1H-imidazol-1-yl)phenyl)benzo[d]thiazole (8b);
2-(4-(5-(1H-Indol-3-yl)-1H-imidazol-1-yl)phenyl)-6-methoxybenzo[d]thiazole (9a);
6-Methoxy-2-(4-(5-(5-methoxy-1H-indol-3-yl)-1H-imidazol-1-yl)phenyl)benzo[d]thiazole (9b);
2-(4-(5-(1H-Indol-3-yl)-1H-imidazol-1-yl)phenyl)-5,7-dimethoxybenzo[d]thiazole (10a);
5,7-Dimethoxy-2-(4-(5-(5-methoxy-1H-indol-3-yl)-1H-imidazol-1-yl)phenyl)benzo[d]thiazole (10b);
2-(4-(5-(1H-Indol-3-yl)-1H-imidazol-1-yl)phenyl)-5,6,7-trimethoxybenzo[d]thiazole (11a);

5,6,7-Trimethoxy-2-(4-(5-(5-methoxy-1H-indol-3-yl)-1H-imidazol-1-yl)phenyl)benzo[d]thiazole (11b);

6-Fluoro-2-(4-(5-(5-nitro-1H-pyrrol-2-yl)-1H-imidazol-1-yl)phenyl)benzo[d]thiazole (12a);

6-Fluoro-2-(4-(5-(5-nitrothiophen-2-yl)-1H-imidazol-1-yl)phenyl)benzo[d]thiazole (12b);

6-Methoxy-2-(4-(5-(5-nitro-1H-pyrrol-2-yl)-1H-imidazol-1-yl)phenyl)benzo[d]thiazole (13a);

6-Methoxy-2-(4-(5-(5-nitrothiophen-2-yl)-1H-imidazol-1-yl)phenyl)benzo[d]thiazole (13b);

5,7-Dimethoxy-2-(4-(5-(5-nitro-1H-pyrrol-2-yl)-1H-imidazol-1-yl)phenyl)benzo[d]thiazole (14a);

5,7-Dimethoxy-2-(4-(5-(5-nitrothiophen-2-yl)-1H-imidazol-1-yl)phenyl)benzo[d]thiazole (14b);

5,6,7-Trimethoxy-2-(4-(5-(5-nitro-1H-pyrrol-2-yl)-1H-imidazol-1-yl)phenyl)benzo[d]thiazole (15a);

5,6,7-Trimethoxy-2-(4-(5-(5-nitrothiophen-2-yl)-1H-imidazol-1-yl)phenyl)benzo[d]thiazole (15b).

In yet another embodiment of the resent invention, structural formulae of the representative compounds are:

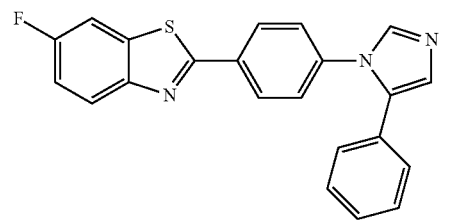
4a

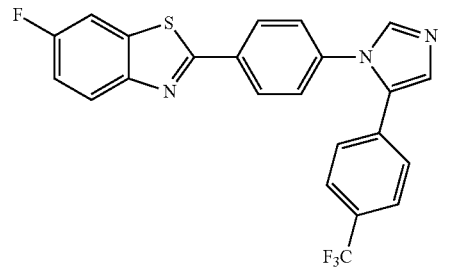
4b

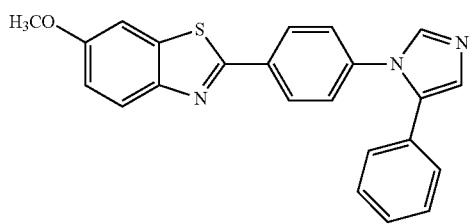
5a

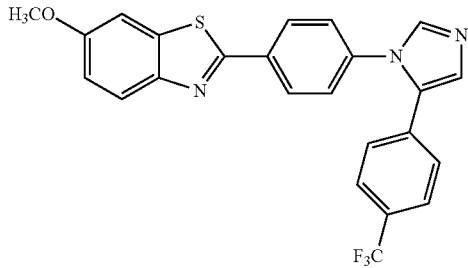
5b

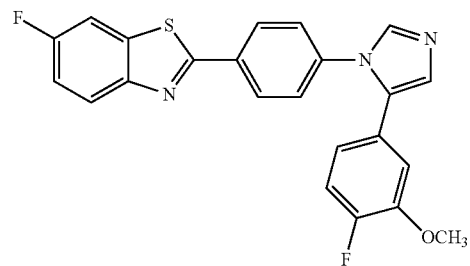
4c

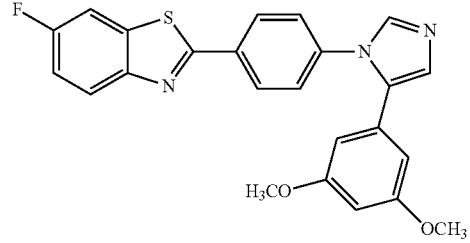
4d

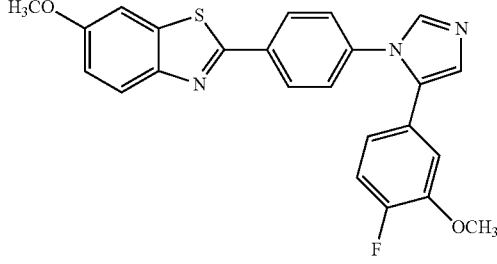
5c

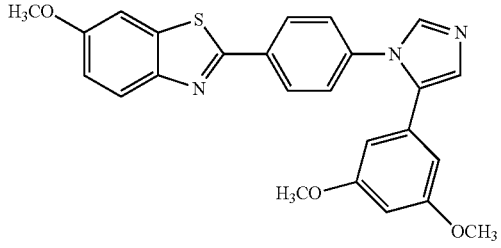
5d

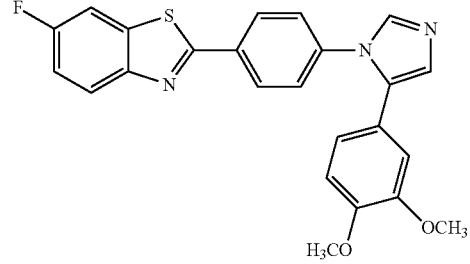
4e

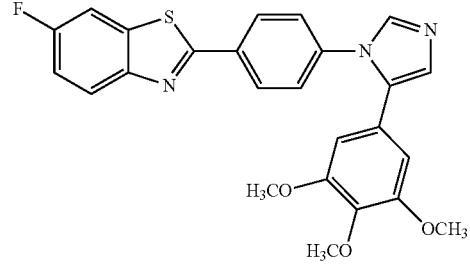
4f

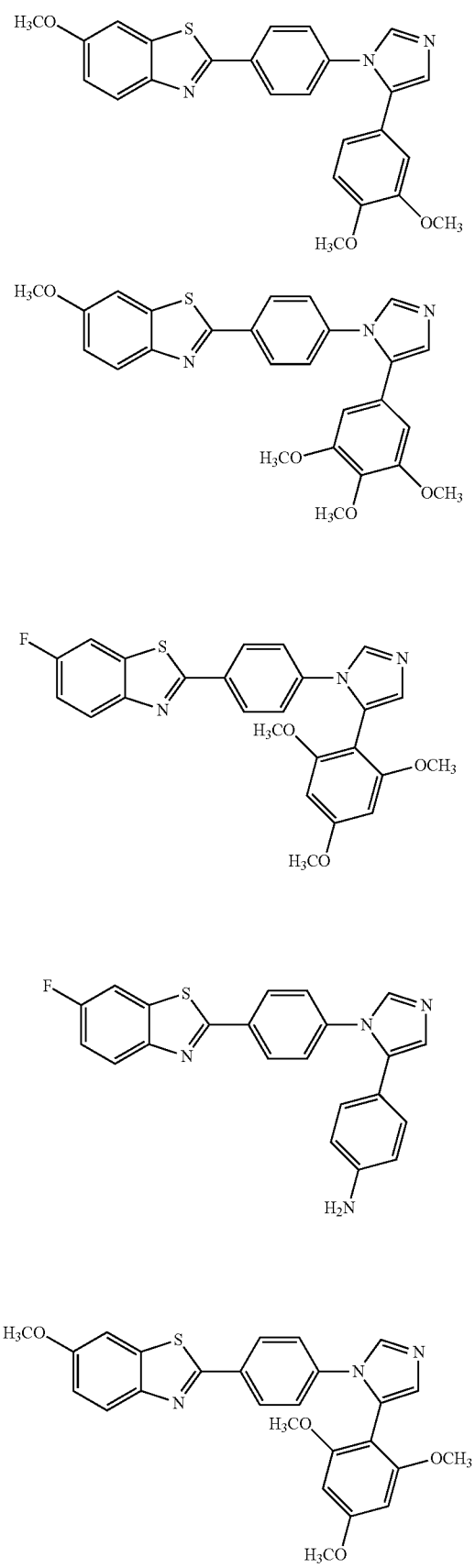
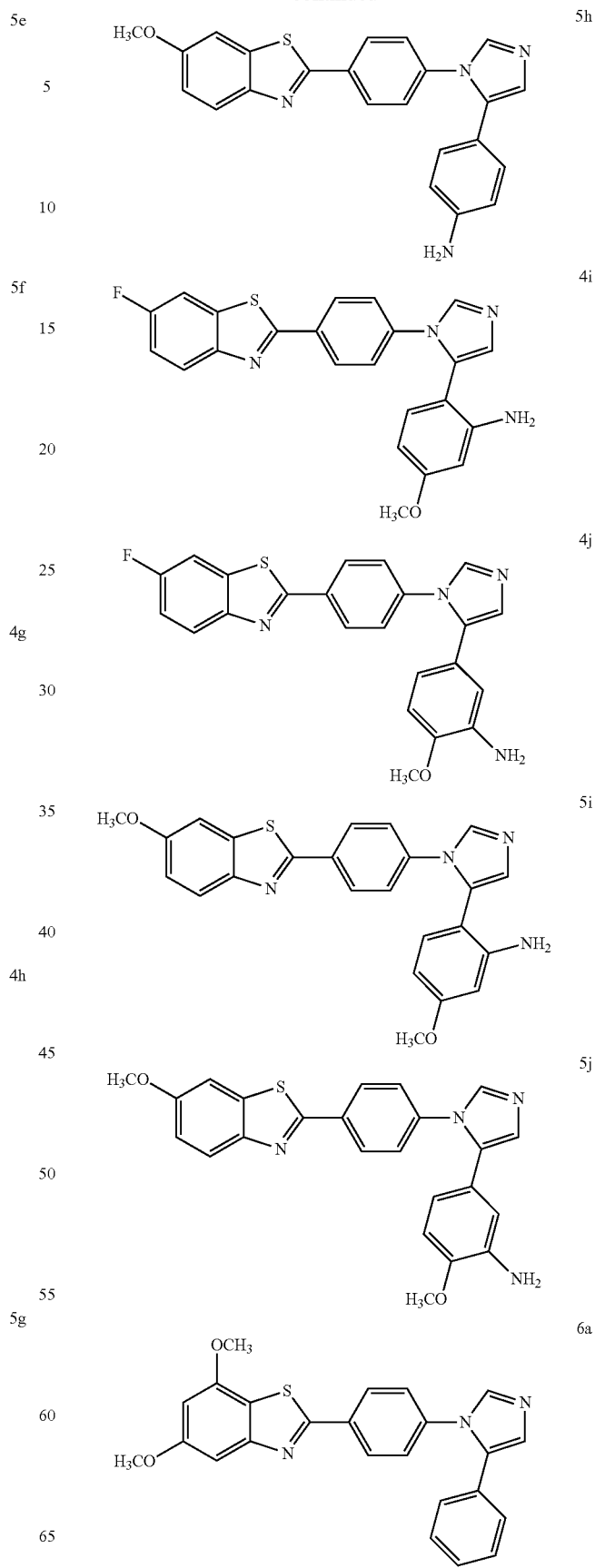

6b
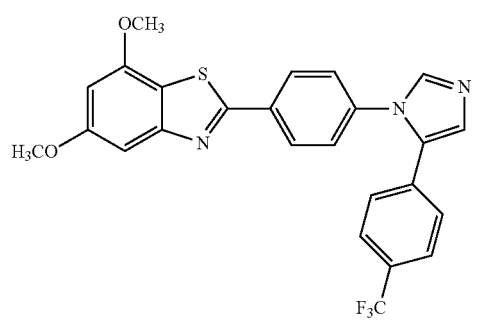
7a
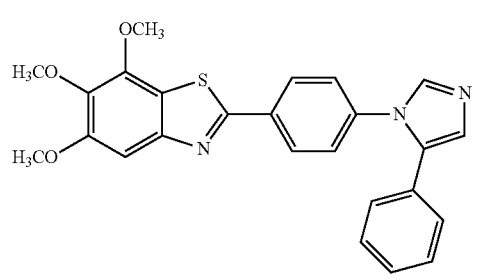
7b
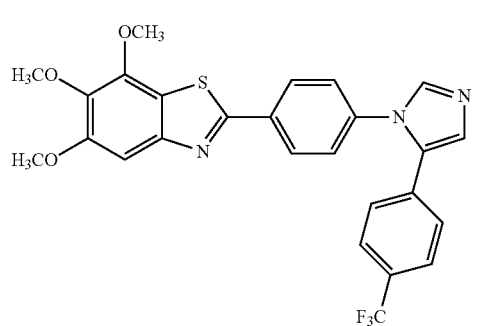
6c
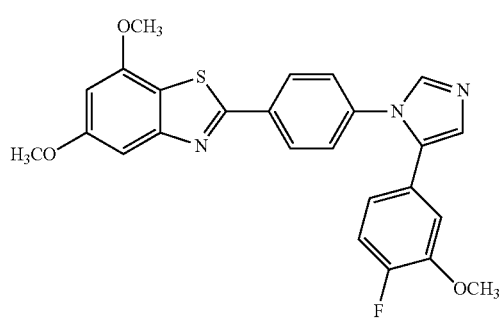
6d
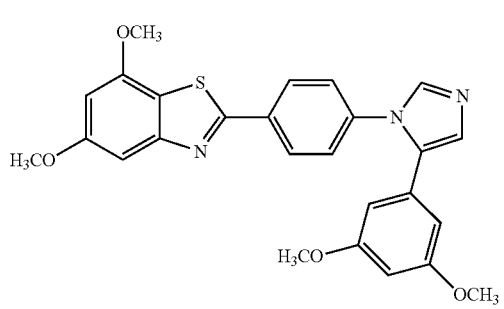
7c
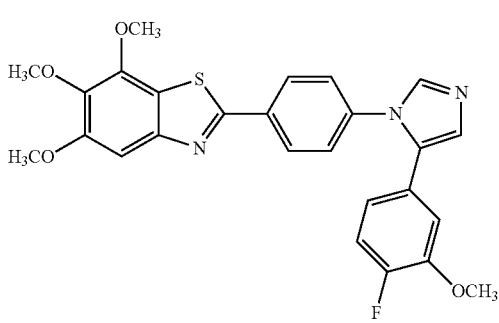
7d
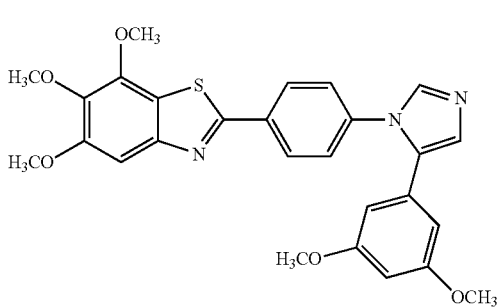
6e
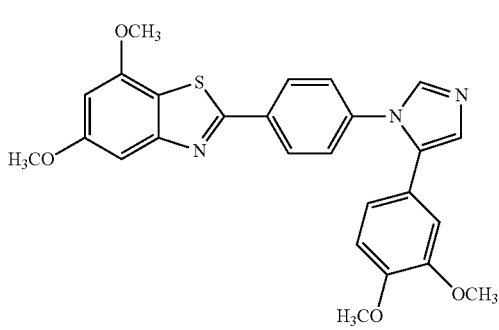
6f
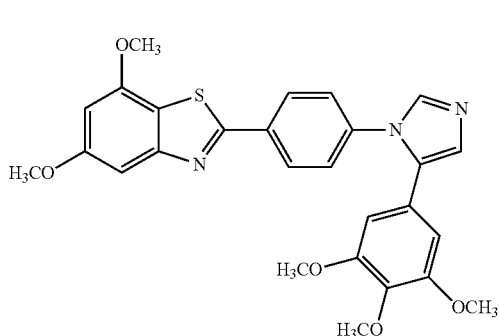
7e
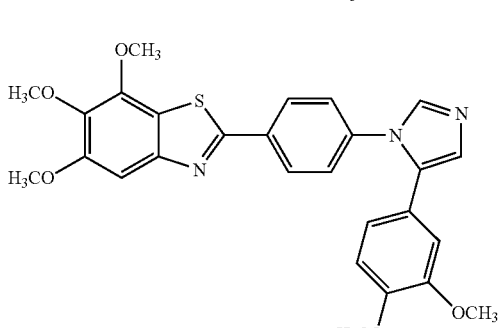

15
-continued
7f
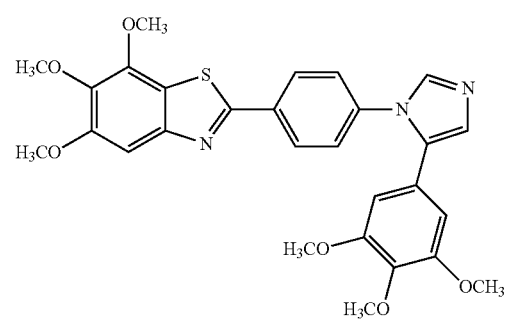
6g
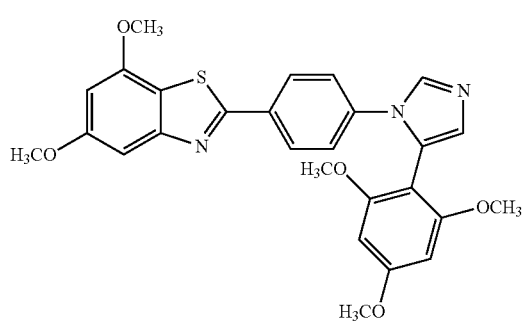
6h
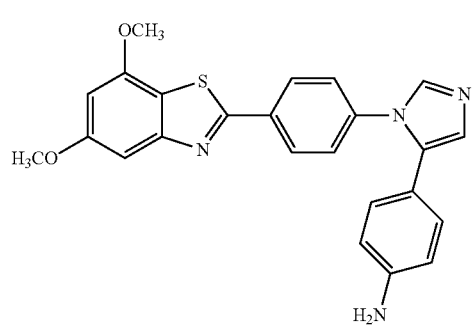
7g
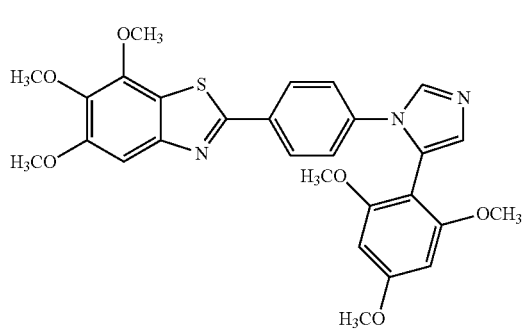
7h
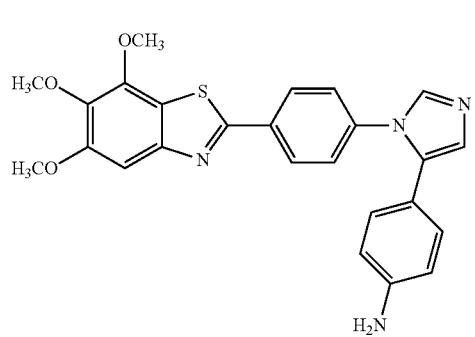
16
-continued
6i
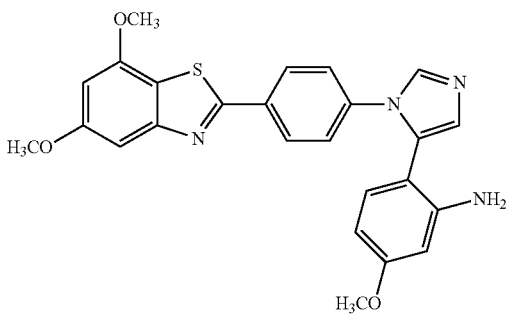
6j
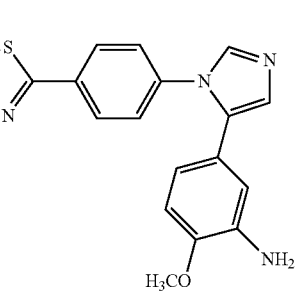
7i
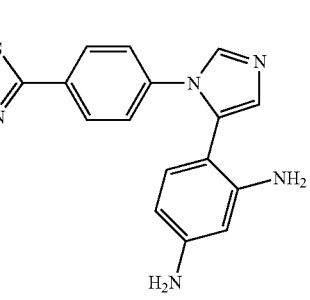
7j
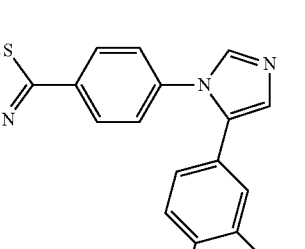
8a
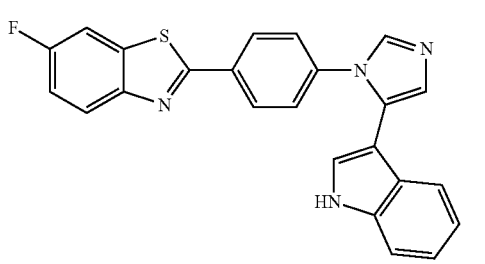

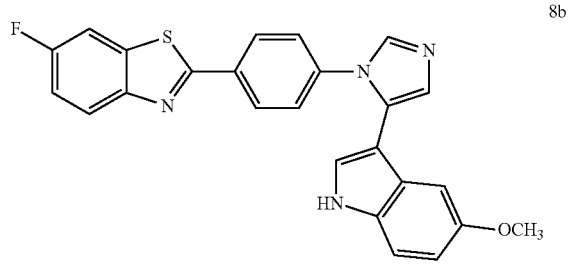
8b
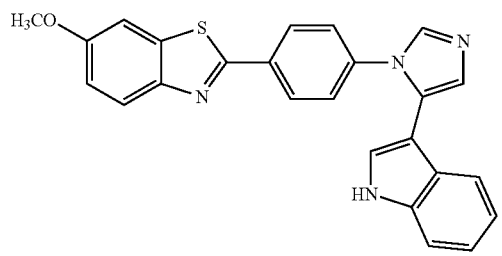
9a
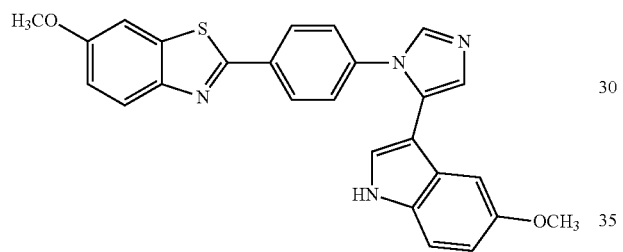
9b
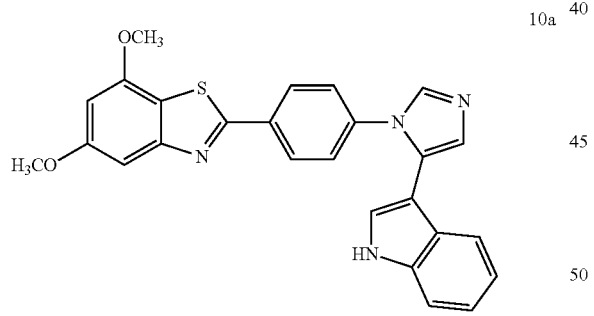
10a
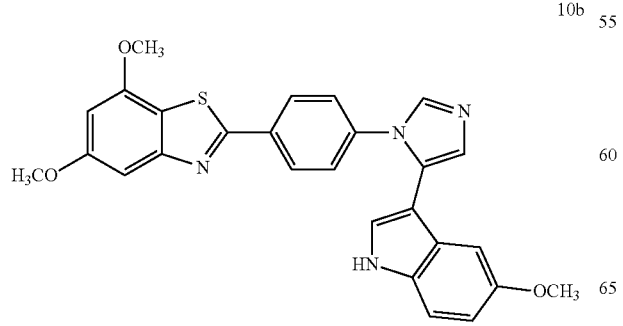
10b
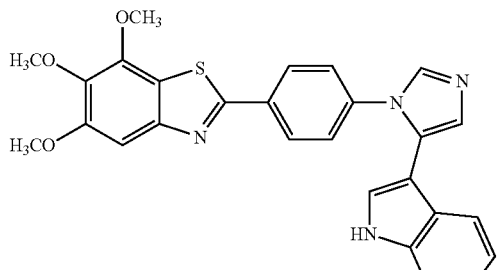
11a
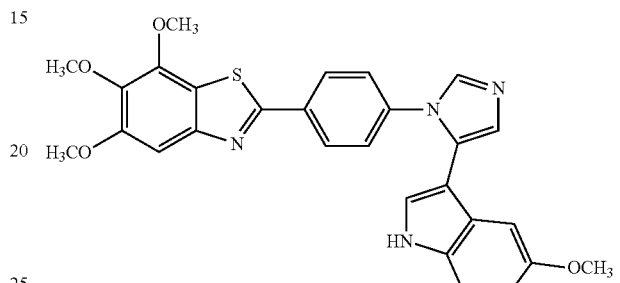
11b
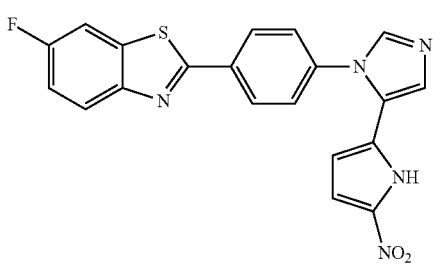
12a
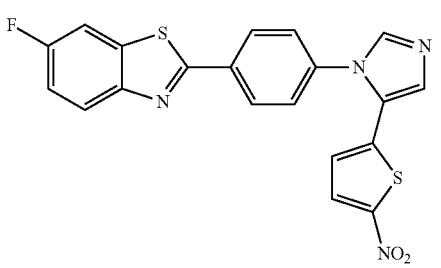
12b
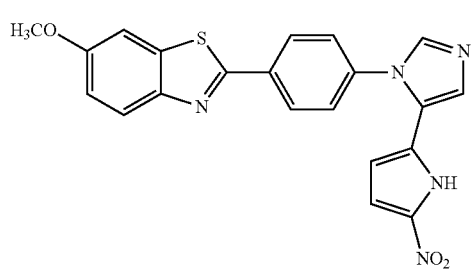
13a

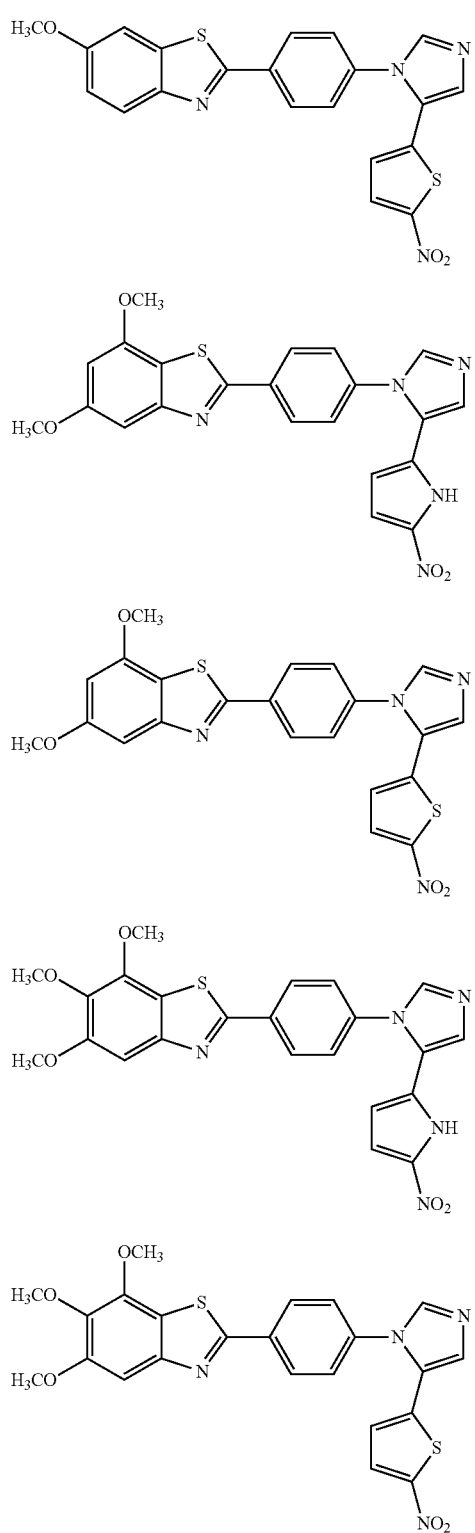

In yet another embodiment of the present invention, said 2-phenyl benzothiazole linked imidazole compounds are useful as anticancer agent.

In yet another embodiment of the present invention, compounds of formula 4c, 6d, 6e, 6f, 7d, 7h and 7j exhibiting an in vitro anticancer activity against sixty human cancer cell lines, derived from nine cancer cell types leukemia cell line, non small cell lung cell line, colon cell line, CNS cell line, renal cell line, prostate cell line, ovarian cell line, breast and melanoma cell line.

In yet another embodiment of the present invention, compounds of formula 4c, 6d, 6e, 6f, 7d, 7h and 7j exhibiting an in vitro anticancer activity against six leukemia cancer cell lines (CCRF-CEM, HL-60, K-562, MOLT-4, SR and RPMI-8226) for $GI_{50}$ are in the range of 2.50 to 6.92, 3.22 to 3.30, 3.03 to 5.88, 3.24 to 5.39, 2.43 to 7.14, 0.989 to 1.40, and 2.20 to 4.00 µM respectively at an exposure period of at least 48 h.

In yet another embodiment of the present invention, compounds of formula 4c, 6d, 6e, 6f, 7d, 7h and 7j exhibiting an in vitro anticancer activity against nine Non-small cell lung cancer cell line (A549/ATCC, EKVX, HOP-62, HOP-92, NCI-H226, NCI-H23, NCI-H322M, NCI-H460 and NCI-H522) for $GI_{50}$ are in the range of 5.47 to 49.3, 2.49 to 18.5, 5.26 to 41.8, 3.27 to 75.9, 1.87 to 86.5, 0.446 to 5.13, and 3.37 to 25.7 µM respectively at an exposure period of at least 48 h.

In yet another embodiment of the present invention, compounds of formula 4c, 6d, 6e, 6f, 7d, 7h and 7j exhibiting an in vitro anticancer activity against seven colon cancer cell line (COLO 205, HCC-2998, HCT-116, HCT-15, HT29, KM12 and SW-620) for $GI_{50}$ are in the range of 4.36 to 82.3, 4.52 to 4.93, 5.48 to 7.13, 3.92 to 5.96, 3.76 to 13.7, 2.79 to 3.81, and 2.94 to 6.21 µM respectively at an exposure period of at least 48 h.

In yet another embodiment of the present invention, compounds of formula 4c, 6d, 6e, 6f, 7d, 7h and 7j exhibiting an in vitro anticancer activity against six CNS cancer cell line (SF-268, SF-295, SF-539, SNB-19, SNB-75 and U251) for $GI_{50}$ are in the range of 12.6 to 75.9, 2.40 to 11.3, 7.00 to 9.96, 4.15 to 8.59, 3.64 to 22.1, 1.53 to 12.3, and 4.44 to 52.3 µM respectively at an exposure period of at least 48 h.

In yet another embodiment of the present invention, compounds of formula 4c, 6d, 6e, 6f, 7d, 7h and 7j exhibiting an in vitro anticancer activity against eight renal cancer cell line (786-0, A498, ACHN, CAM-1, SN12C, TK-10 UO-31 and RXF 393) for $GI_{50}$ are in the range of 0.0432 to 38.8, 2.13 to 16.8, 2.15 to 3.17, 1.83 to 9.40, 1.94 to 31.9, 1.41 to 8.95, and 1.99 to 9.44 µM respectively at an exposure period of at least 48 h.

In yet another embodiment of the present invention, compounds of formula 4c, 6e, 6f, 7d, 7h and 7j exhibiting an in vitro anticancer activity against two prostate cancer cell line (PC-3, DU-145) for $GI_{50}$ are 3.47 to 14.3, 3.66 to 27.9, 2.54, 3.17 to 31.1, 3.02 to 7.25, and 2.59 to 6.38 µM respectively at an exposure period of at least 48 h.

In yet another embodiment of the present invention, compounds of formula 4c, 6d, 6e, 6f, 7d, 7h and 7j exhibiting an in vitro anticancer activity against seven ovarian cancer cell line (IGROV1, OVCAR-3, OVCAR-4, OVCAR-5, OVCAR-8, NCI/ADR-RES and SK-OV-3) for $GI_{50}$ are in the range of 5.71 to 30.6, 2.87 to 14.5, 3.85 to 56.1, 3.25 to 5.87, 6.07 to 49.9, 1.61 to 34.3, and 3.12 to 6.29 µM respectively at an exposure period of at least 48 h.

In yet another embodiment of the present invention, compounds of formula 4c, 6d, 6e, 6f, 7d, 7h and 7j exhibiting an in vitro anticancer activity against six breast cancer cell line (MCF7, MDA-MB-231/ATCC, HS 578T, BT-549, TD-47D and MDA-MB-468) for $GI_{50}$ are in the range of 7.98 to 32.2, 3.09 to 9.01, 3.78 to 28.4, 3.27 to 5.23, 4.02 to 20.9, 1.59 to 5.36, and 3.02 to 28.3 µM respectively at an exposure period of at least 48 h.

In yet another embodiment of the present invention, compounds of formula 4c, 6d, 6e, 6f, 7d, 7h and 7j exhibiting an in vitro anticancer activity against nine melanoma cancer cell line (LOX IMVI, MALME-3M, M14, MDA-MB-435, SK-MEL-2, SK-MEL-28, SK-MEL-5, UACC-257 and UACC-62) for $GI_{50}$ are in the range of 4.11 to 39.7, 1.53 to 9.69, 3.61 to 59.8, 2.46 to 7.91, 2.85 to 31.6, 0.710 to 6.40, and 1.73 to 13.7 μM respectively at an exposure period of at least 48 h.

In yet another embodiment of the present invention, compounds of formula 4c, 6d, 6e, 6f, 7d, 7h and 7j exhibiting mean graph midpoint values (MG_MID) of $\log_{10}GI_{50}$ to all the cell lines are in the range of −5.38 to −4.52, −5.48 to −4.0, −5.13 to −4.39, −5.42 to −4.78, −5.43 to −4.82, −5.92 to −5.24 and −5.49 to −4.53 respectively at an exposure period of at least 48 h.

In yet another embodiment of the present invention, compounds of formula 4c, 6d, 6e, 6f, 7d, 7h and 7j exhibiting mean graph midpoint values (MG_MID) of $\log_{10}LC_{50}$ to all the cell lines are in the range of −4.00 to −4.03, −4.00, −4.00, −4.00, −4.00 to −4.18, −4.00 to −4.09, −4.00 respectively at an exposure period of at least 48 h.

In yet another embodiment of the present invention, compounds of formula 4c, 6d, 6e, 6f, 7d, 7h and 7j exhibiting mean graph midpoint values (MG_MID) of $\log_{10}TGI$ to all the cell lines are in the range of −4.00 to −4.41, −4.00 to −4.19, −4.00 to −4.06, −4.00, −4.00 to −4.54, −4.00 to −4.26 and −4.00 to −4.11 respectively at an exposure period of at least 48 h.

In an embodiment, a process for the preparation of 2-phenyl benzothiazole linked imidazole compounds of general formula A comprising the steps of:

i. adding 4-nitrobenzoyl chloride (17) to a stirred solution of substituted anilines (16a-d) in the ratio ranging between 1.5:1 to 1:1 in pyridine and reflux for 2 to 3h to obtain coupled amide of formula 18a-d;

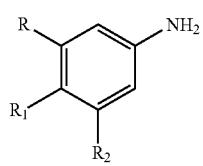

16a-d

R = hydrogen or methoxy;
$R_1$ = hydrogen, methoxy or fluoro;
$R_2$ = hydrogen or methoxy;

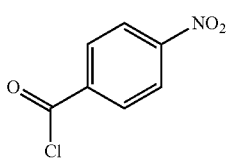

17

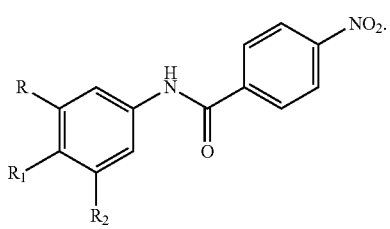

18a-d

R = hydrogen or methoxy;
$R_1$ = hydrogen, methoxy or fluoro;
$R_2$ = hydrogen or methoxy ii. treating the amide of formula (18a-d) as obtained in step (i) with Lawesson's reagent, in toluene under reflux conditions for 6 to 8 hr to obtain the corresponding thioamides (19a-d);

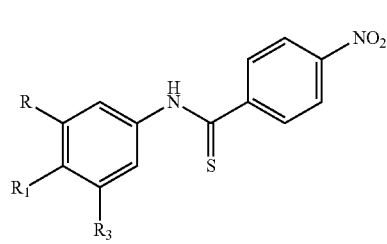

19a-d iii. treating thioamides (19a-d) as obtained in step (ii) with potassium ferricyanide (1:4) in aqueous sodium hydroxide solution under reflux conditions for 2 to 3h to obtain the substituted 2-(4-nitro phenyl benzothiazole) of formula 20a-d;

iv. reducing substituted 2-(4-nitro phenyl benzothiazole) of formula 20a-d with $SnCl_2.2H_2O$ to obtain amine compounds (21a-d);

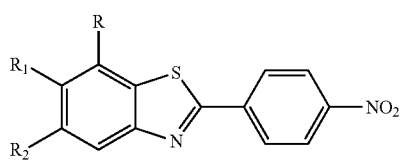

20a-d

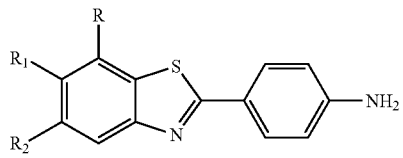

21a-d v. treating amine compounds (21a-d) as obtained in step (iv) with substituted aldehydes in the presence of catalytic amount of acetic acid (2-3 drops) in 15 to 20 mL of ethanol solution under reflux conditions to obtain imine compounds followed by treatment with p-toulenesulfonyl methy isocyanide to obtain nitro intermediates (25a-l) and compound of formula 4a-g to 7a-g and 8a-b to 15a-b;

vi. reducing nitro intermediate as obtained in step (v) with $SnCl_2.2H_2O$ in ethanol to obtain compound of formula 4h-j to 7h-j.

25 a-I

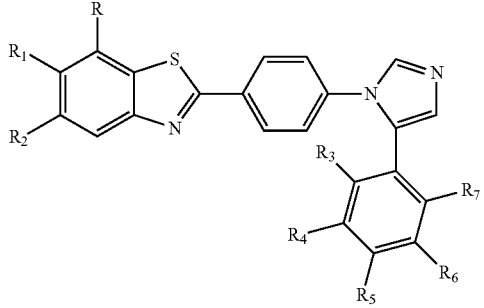

25a R$_3$ = R$_4$ = R$_6$ = R$_7$ = H; R$_6$ = NO$_2$; R = R$_2$ = H; R$_1$ = F
25b: R$_4$ = R$_6$ = R$_7$ = H; R$_3$ = NO$_2$; R$_5$ = OCH$_3$; R = R$_2$ = H; R$_1$ = F
25c: R$_3$ = R$_6$ = R$_7$ = H; R$_4$ = NO$_2$; R$_5$ = OCH$_3$; R = R$_2$ = H; R$_1$ = F
25d: R$_3$ = R$_4$ = R$_6$ = R$_7$ = H; R$_5$ = NO$_2$; R = R$_2$ = H; R$_1$ = OCH$_3$
25e: R$_4$ = R$_6$ = R$_7$ = H; R$_3$ = NO$_2$; R$_5$ = OCH$_3$; R = R$_2$ = H; R$_1$ = OCH$_3$
25f: R$_3$ = R$_6$ = R$_7$ = H; R$_4$ = NO$_2$; R$_5$ = OCH$_3$; R = R$_2$ = H; R$_1$ = OCH3
25g: R$_3$ = R$_4$ = R$_6$ = R7 = H; R$_5$ = NO$_2$; R = R$_2$ = OCH$_3$; R$_1$ = H
25h: R$_4$ = R$_6$ = R$_7$ = H; R$_3$ = NO$_2$; R$_5$ = OCH$_3$; R = R$_2$ = OCH$_3$; R$_1$ = H$_3$
25i: R$_3$ = R$_6$ = R$_7$ = H; R$_4$ = NO$_2$; R$_5$ = OCH$_3$; R = R$_2$ = OCH$_3$; R$_1$ = H
25j: R$_3$ = R$_4$ = R$_6$ = R$_7$ = H; R$_5$ = NO$_2$; R = R1 = R$_2$ = OCH$_3$;
25k: R$_4$ = R$_6$ = R$_7$ = H; R$_3$ = NO$_2$; R$_5$ = OCH$_3$; R = R$_1$ = R$_2$ = OCH$_3$;
25l: R$_3$ = R$_6$ = R$_7$ = H; R$_4$ = NO$_2$; R$_5$ = OCH$_3$; R = R$_1$ = R$_2$ = OCH$_3$;

vii. purifying compound of formula 4a-g to 7a-g and 8a-b to 15a-b as obtained in step (v) and 4h-j to 7h-j as obtained in step (vi) by column chromatography using solvent to obtain final compounds of general formula 1.

In yet another embodiment of the present invention, substituted aldehydes used is selected from the group consisting of 22a-j, 23a-b and 24a-b.

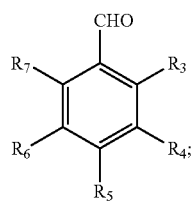

22a-j

22a: R$_3$ = R$_4$ = R$_5$ = R$_6$ = R$_7$ = H;
22b: R$_3$ = R$_4$ = R$_5$ = R$_6$ = R$_7$ = H; R$_5$ = CF$_3$
22c: R$_3$ = R$_6$ = R$_7$ = H; R$_4$ = OCH$_3$ R$_5$ = F
22d: R$_3$ = R$_5$ = R$_7$ = H; R$_4$ = R$_6$ = OCH$_3$
22e: R$_3$ = R$_6$ = R$_7$ = H; R$_4$ = R$_5$ = OCH$_3$
22f: R$_3$ = R$_7$ = H; R$_4$ = R$_5$ = R$_6$ = OCH$_3$
22g: R$_4$ = R$_6$ = H; R$_3$ = R$_5$ = R$_7$ = OCH$_3$
22h: R$_3$ = R$_4$ = R$_6$ = R$_7$ = H; R$_5$ = NO$_2$
22i: R$_4$ = R$_6$ = R$_7$ = H; R$_3$ = NO$_2$; R$_2$ = OCH$_3$
22j: R$_3$ = R$_6$ = R$_7$ = H; R$_4$ = NO$_2$; R$_5$ = OCH$_3$

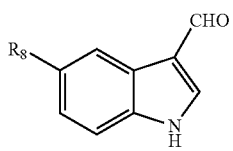

23a-b

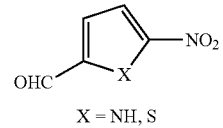

24a-b

X = NH, S

23a: R$_8$ = H;
23b: R$_8$ = OCH$_3$
24a: X = NH;
24b: X = S

In yet another embodiment of the present invention, solvent used are selected from ethyl acetate, hexane, chloroform or methanol.

Figure 4:
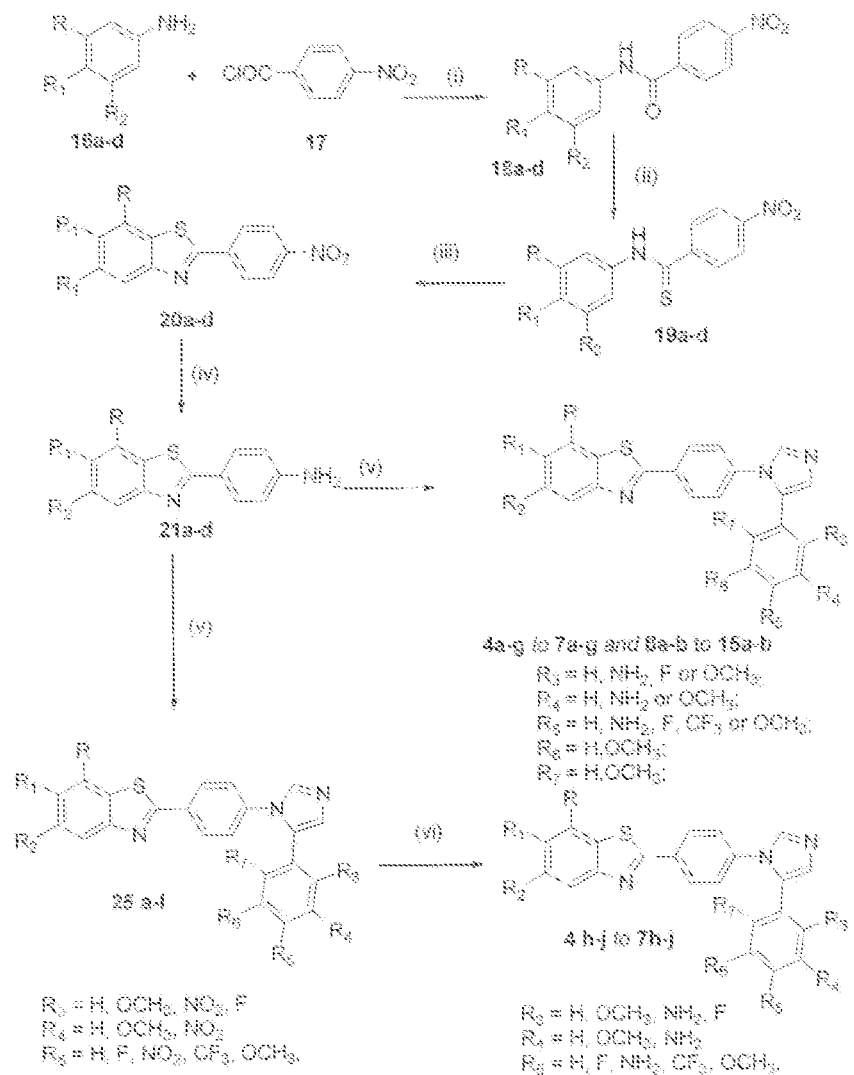
FIG. 4 represents schematic diagram for the preparation of compound of general formula A wherein reagent and conditions are (i) Pyridine, reflux, 2h; (ii) Lawessons reagent, toluene, reflux, 8h; (iii) K3[FeCN)$_6$], Aq.NaOH, 2H; (IV) SnCl$_2$.2H$_2$O, ethanol, reflux, 2h; (v)ethanol, AcOH (Cat), reflux; (vi) p-toluene sulfonyl methyl isocyanide, K$_2$CO$_3$, DME:MEOH (1:2) reflux, 12h; (vii) SnCl$_2$.2H$_2$O, ethanol, reflux, 2h.

DETAILED DESCRIPTION OF THE INVENTION 2-phenyl benzothiazole linked imidazole compounds have shown promising anticancer activity in various cell lines. The molecules synthesized are of immense biological significance with potential inhibition of tubulin polymerization. This resulted in design and synthesis of new congeners as illustrated in FIG. 4, which comprise:
1. Coupling reaction between substituted anilines and 4-nitro benzoyl chloride;
2. Conversion of amide compound into corresponding thioamide using lawessons reagent in toluene at reflux conditions for 6 to 8h;
3. Benzothiazole ring cyclization takes place in the presence of K$_3$[Fe(CN)$_6$] and in aqueous NaOH for 2 to 3h under reflux conditions;
4. Reduction of nitro group of 4-nitro 2-phenyl benzothiazole by SnCl$_2$.2H$_2$O to form amine compounds;
5. Reaction of amines with substituted aldehydes in the presence of catalytic amount of acetic acid in ethanol solution under reflux conditions afforded imine formation with on reaction with p-toulenesulfonyl methyl isocyanide (Tosmic) and base K$_2$CO$_3$ using solvents DME:MeOH (1:4) under reflux conditions for 12 h yielded the corresponding 2-phenyl benzothiazole linked imidazole compounds and also some nitro intermediates which obtained by the reaction of nitro substituted aldehydes under above conditions further on reduction with SnCl$_2$.2H$_2$O to obtain final compounds containing amine functionality which exhibiting promising anticancer activity in various cell lines;

6. Purification by column chromatography using different solvents like ethyl acetate, hexane, chloroform and methanol.

EXAMPLES

Following examples are given by way of illustration therefore should not construed to limit the scope of the invention.

Example 1

6-fluoro-2-(4-(5-(4-fluoro-3-methoxyphenyl)-1H-imidazol-1-yl)phenyl)benzo[d]thiazole (4c)

To a stirred solution of 4-fluoro aniline (16a, 4g, 32.7 mmol) in pyridine as solvent and base to this 4-nitrobenzoyl chloride (17, 6.69 g, 36.0 mmol) is added slowly and reflux for 2h, after completion of the reaction, reaction mixture is poured in water, filter and washed with dil HCl to afford compound N-(4-fluorophenyl)-4-nitrobenzamide (18a). To a stirred solution of amide (18a, 8g, 30.7 mmol) taken in toluene lawessons reagent (2,4-bis(4-methoxyphenyl)-1,3,2,4-dithiadiphosphetane-2,4-disulfide) (10.18 g, 25.2 mmol) is added and refluxed at 110° C. for 7h. After completion of the reaction toluene is evaporated under vacuum and water is added and extracted into chloroform finally purification by column chromatography to afford pure compound N-(4-fluorophenyl)-4-nitrobenzothioamide (19a). Treating the thioamide product (19a, 4g, 14.49 mmol) with potassium ferricyanide (4 eq) in aqueous sodium hydroxide (8 eq) solution at 90° C. for 3h cyclization takes place to obtain the 6-fluoro-2-(4-nitrophenyl)benzo[d]thiazole (20a) solid is precipitated from the reaction mixture filtered and washed with water to get 20a. Reduction of the nitro compound (20a, 1 g, 3.64 mmol) is proceeded with SnCl$_2$.2H$_2$O in ethanol and reflux at 80° C. for 2h. After completion of reaction ethanol is evaporated under vacuum and to this saturated sodium bicarbonate solution is added to quench the excess stannous chloride and filtered in celite bed and purified in silica column (60-120) to afforded pure compound (21a) The compound 4-(6-fluorobenzo[d]thiazol-2-yl)benzenamine (21a, 244 mg, 1 mmol) on reaction with 4-fluoro 3-methoxy benzaldehyde (22c, 152 mg, 1 mmol) in ethanol using catalytic amount of acetic acid and refluxed for 2h after completion reaction mixture is cooled to 0° C. solid is precipitated from the reaction mixture it is filtered and washed with ethanol to gave the enamine product, and immediately proceeded for the next reaction with using (p-tolylsulfonyl) methyl isocyanide (tosmic) (1.5 eq), and potassium carbonate (2 eq) as base, in 10 mL of methanol and 5 mL of DME was heated under reflux for 12 h after completion of reaction as monitored by TLC. It was cooled to room temperature (27° C.); the solution was concentrated in vacuo and partitioned between EtOAc and water. The organic layer was separated, washed with brine, dried over anhydrous sodium sulfate, filtered, and concentrated in vacuo. The residue was purified by flash chromatography on silica gel eluting with EtOAc and Hexane to gave compound 4c as a light yellow solid (68%).

1H NMR (CDCl$_3$, 300 MHz): δ 8.11 (d, 2H, J=8.3 Hz), 8.02 (q, 1H, J=4.5 Hz), 7.76 (s, 1H), 7.58 (dd, 1H, J=6.0, 2.2 Hz), 7.29 (d, 2H, J=8.3 Hz), 7.25 (m, 2H), 6.98 (q, 1H, J=8.3, 3.0 Hz), 6.73 (dd, 1H, J=2.2 Hz, 6.0 Hz), 6.68 (m, 1H), 3.70 (s, 3H), ESI-MS: m/z 420 [M+1]$^+$.

Example 2

2-(4-(5-(3,5-dimethoxyphenyl)-1H-imidazol-1-yl)phenyl)-5,7-dimethoxybenzo[d]thiazole (6d)

To a stirred solution of 3,5-dimethoxybenzenamine (16c, 4g, 26.1 mmol) in pyridine as solvent and base to this 4-nitrobenzoyl chloride (17, 5.3 g, 28.7 mmol) is added slowly and reflux for 2h, after completion of the reaction, reaction mixture is poured in water, filtered, washed with dil HCl and dried to afford compound N-(3,5-dimethoxyphenyl)-4-nitrobenzamide (18c). To a stirred solution of amide (18c, 5g, 16.5 mmol) taken in toluene to this lawessons reagent (4.6 g, 11.5 mmol) is added and refluxed at 110° C. for 8h. After completion of the reaction toluene is evaporated under vacuum and water is added and extracted into chloroform and finally purified by column chromatography to afford pure compound N-(3,5-dimethoxyphenyl)-4-nitrobenzothioamide (19c). Treating the thioamide product (19c, 3g, 9.4 mmol) with potassium ferricyanide (4 eq) in aqueous sodium hydroxide (8 eq) solution at 90° C. for 2h cyclization takes place to obtain the 5,7-dimethoxy-2-(4-nitrophenyl)benzo[d]thiazole (20c) solid is precipitated from the reaction mixture filtered and washed with water and dried to afforded product 20c. Reduction of the nitro compound (20c, 500 mg, 1.5 mmol) is proceeded with SnCl$_2$.2H$_2$O in ethanol and reflux at 80° C. for 2h, after completion of reaction ethanol is evaporated under vacuum and to this saturated sodium bicarbonate solution is added to quench the excess stannous chloride and filtered in celite bed and purified in silica column (60-120) to afforded pure compound (21c). The compound 4-(5,7-dimethoxybenzo[d]thiazol-2-yl)benzenamine (21c, 200 mg, 0.698 mmol) on reaction with 3,5-dimethoxybenzaldehyde (22d, 116 mg, 0.698 mmol) in ethanol using catalytic amount of acetic acid and refluxed for 2h after completion reaction mixture is cooled to 0° C. solid is precipitated from the reaction mixture it is filtered and washed with ethanol to gave the enamine product, and immediately proceeded for the next reaction by using (p-tolylsulfonyl) methyl isocyanide (tosmic) (1.5 eq), and potassium carbonate (2 eq) as base, in 10 mL of methanol and 5 mL of DME was heated under reflux for 12 h after completion of reaction as monitored by TLC. It was cooled to room temperature (27° C.); the solution was concentrated in vacuo and partitioned between EtOAc and water. The organic layer was separated, washed with brine, dried over anhydrous sodium sulfate, filtered, and concentrated in vacuo. The residue was purified by flash chromatography on silica gel eluting with EtOAc and Hexane to gave compound 6d as a brown solid (63%).

$^1$H NMR (CDCl$_3$, 500 MHz): δ 8.10 (d, 2H J=8.2 Hz), 7.75 (d, 1H) 7.30 (d, 2H, J=8.2), 7.29 (s, 1H), 7.17 (d, 1H, J=1.8 Hz), 6.51 (s, 1H), 6.37 (t, 1H), 6.30 (s, 2H) 3.95 (s, 3H), 3.89 (s, 3H), 3.64 (s, 6H); ESI-MS: m/z 474 [M+1]$^+$.

Example 3

2-(4-(5-(3,4-dimethoxyphenyl)-1H-imidazol-1-yl)phenyl)-5,7-dimethoxybenzo[d]thiazole (6e)

To a stirred solution of 3,5-dimethoxybenzenamine (16c, 4g, 26.1 mmol) in pyridine as solvent and base to this 4-nitrobenzoyl chloride (17, 5.3g, 28.7 mmol) is added slowly and reflux for 2h, after completion of the reaction, reaction mixture is poured in water, filter and washed with dil HCl and dried to afford compound N-(3,5-dimethoxyphenyl)-4-nitrobenzamide (18c). To a stirred solution of amide (18c, 5g, 16.5 mmol) taken in toluene add lawessons reagent (4.6 g, 11.5 mmol) and refluxed at 110° C. for 6h. After completion of the reaction toluene is evaporated under vacuum and water is added and extracted into chloroform and finally purified by column chromatography to afford pure compound N-(3,5-dimethoxyphenyl)-4-nitrobenzothioamide (19c). Treating the thioamide product (19c, 3g, 9.4 mmol) with potassium ferricyanide (4 eq) in aqueous sodium hydroxide (8 eq) solution at 90° C. for 2h cyclization takes place to obtain the 5,7-dimethoxy-2-(4-nitrophenyl)benzo[d]thiazole (20c) solid is precipitated from the reaction mixture filtered and washed with water and dried to afforded product 20c. Reduction of the nitro compound (20c, 500 mg, 1.5 mmol) is proceeded with $SnCl_2.2H_2O$ in ethanol and reflux at 80° C. for 2h, after completion of reaction ethanol is evaporated under vacuum and to this saturated sodium bicarbonate solution is added to quench the excess stannous chloride and filtered in celite bed and purified in silica column (60-120) to afforded pure compound (21c). The compound 4-(5,7-dimethoxybenzo[d]thiazol-2-yl)benzenamine (21c, 200 mg, 0.698 mmol) on reaction with 3,4-dimethoxybenzaldehyde (22e, 116 mg, 0.698 mmol) in ethanol using catalytic amount of acetic acid and refluxed for 2h after completion reaction mixture is cooled to 0° C. solid is precipitated from the reaction mixture it is filtered and washed with ethanol to gave the enamine product, and immediately proceeded for the next reaction by using (p-tolylsulfonyl) methyl isocyanide (tosmic) (1.5 eq), and potassium carbonate (2 eq) as base, in 10 mL of methanol and 5 mL of DME was heated under reflux for 12 h after completion of reaction as monitored by TLC. It was cooled to room temperature (27° C.); the solution was concentrated in vacuo and partitioned between EtOAc and water. The organic layer was separated, washed with brine, dried over anhydrous sodium sulfate, filtered, and concentrated in vacuo. The residue was purified by flash chromatography on silica gel eluting with EtOAc and Hexane to gave compound 6e as a light yellow solid (69%).

$^1H$ NMR ($CDCl_3$, 500 MHz): δ 8.09 (d, 2H J=8.7 Hz), 7.73 (s, 1H), 7.29 (d, 2H, J=8.7 Hz), 7.22 (s, 1H), 7.16 (s, 1H), 6.76 (d, 1H, J=8.7 Hz), 6.72 (dd, 1H, J=6.8, 1.9 Hz), 6.65 (d, 1H, J=1.9 Hz), 6.50 (s, 1H), 3.97 (s, 3H), 3.90 (s, 3H), 3.86 (s, 3H), 3.67 (s, 3H), ESI-MS: m/z 474 [M+1]$^+$.

Example 4

5,7-dimethoxy-2-(4-(5-(3,4,5-trimethoxyphenyl)-1H-imidazol-1-yl)phenyl)benzo[d]thiazole (6f)

To a stirred solution of 3,5-dimethoxybenzenamine (16c, 4g, 26.1 mmol) in pyridine as solvent and base to this 4-nitrobenzoyl chloride (17, 5.3 g, 28.7 mmol) is added slowly and reflux for 2h, after completion of the reaction, reaction mixture is poured in water, filter and washed with dil HCl and dried to afford compound N-(3,5-dimethoxyphenyl)-4-nitrobenzamide (18c). To a stirred solution of amide (18c, 5g, 16.5 mmol) taken in toluene add lawessons reagent (4.6 g, 11.5 mmol) and refluxed at 110° C. for 7h. After completion of the reaction toluene is evaporated under vacuum and water is added and extracted into chloroform and finally purified by column chromatography to afford pure compound N-(3,5-dimethoxyphenyl)-4-nitrobenzothioamide (19c). Treating the thioamide product (19c, 3g, 9.4 mmol) with potassium ferricyanide (4 eq) in aqueous sodium hydroxide (8 eq) solution at 90° C. for 2h cyclization takes place to obtain the 5,7-dimethoxy-2-(4-nitrophenyl)benzo[d]thiazole (20c) solid is precipitated from the reaction mixture filtered and washed with water and dried to afforded product 20c. Reduction of the nitro compound (20c, 500 mg, 1.5 mmol) is proceeded with $SnCl_2.2H_2O$ in ethanol and reflux at 80° C. for 2h, after completion of reaction ethanol is evaporated under vacuum and to this saturated sodium bicarbonate solution is added to quench the excess stannous chloride and filtered in celite bed and purified in silica column (60-120) to afforded pure compound (21c). The compound 4-(5,7-dimethoxybenzo[d]thiazol-2-yl)benzenamine (21c, 200 mg, 0.698 mmol) on reaction with 3,4,5-trimethoxybenzaldehyde (22f, 137 mg, 1 eq) in ethanol using catalytic amount of acetic acid and refluxed for 2h after completion reaction mixture is cooled to 0° C. solid is precipitated from the reaction mixture it is filtered and washed with ethanol to gave the enamine product and immediately proceeded for the next reaction by using (p-tolylsulfonyl) methyl isocyanide (tosmic) (1.5 eq), and potassium carbonate (2 eq) as base, in 10 mL of methanol and 5 mL of DME was heated under reflux for 12 h after completion of reaction as monitored by TLC. It was cooled to room temperature (27° C.); the solution was concentrated in vacuo and partitioned between EtOAc and water. The organic layer was separated, washed with brine, dried over anhydrous sodium sulfate, filtered, and concentrated in vacuo. The residue was purified by flash chromatography on silica gel eluting with EtOAc and Hexane to gave compound 6f as a yellow solid (53%).

$^1H$ NMR ($CDCl_3$, 500 MHz): δ 8.12 (d, 2H, J=8.3 Hz), 7.69 (s, 1H), 7.32 (d, 2H, J=8.3 Hz), 7.20 (s, 1H), 7.11 (d, 1H, J=2.0 Hz), 6.46 (s, 1H), 6.31 (s, 2H), 3.97 (s, 3H), 3.89 (s, 3H), 3.80 (s, 3H), 3.64 (s, 6H), ESI-MS: m/z 504 [M+1]$^+$.

Example 5

2-(4-(5-(3,5-dimethoxyphenyl)-1H-imidazol-1-yl)phenyl)-5,6,7-trimethoxybenzo[d]thiazole (7d)

To a stirred solution of 3,4,5-trimethoxybenzenamine (16d, 5g, 27.2 mmol) in pyridine as solvent and base to this 4-nitrobenzoyl chloride (17, 5.5g, 29.9 mmol) is added slowly and reflux for 3h, after completion of the reaction, reaction mixture is poured in water, filter and washed with dil HCl and dried to afford compound 4-nitro-N-(3,4,5-trimethoxyphenyl)benzamide (18d). To a stirred solution of amide (18d, 6g, 18.0 mmol) taken in toluene lawessons reagent (5.1g, 12.6 mmol) is added and refluxed at 110° C. for 6h. after completion of the reaction toluene is evaporated under vacuum and water is added and extracted into chloroform and finally purified by column chromatography to afford pure compound 4-nitro-N-(3,4,5-trimethoxyphenyl) benzothioamide (19d). Treating the thioamide product (19d, 4g, 11.4 mmol) with potassium ferricyanide (4 eq) in aqueous sodium hydroxide (8 eq) solution at 90° C. for 2h cyclization takes place to obtain the 5,6,7-trimethoxy-2-(4-nitrophenyl) benzo[d]thiazole (20d) solid is precipitated from the reaction mixture filtered and washed with water and dried to afforded product 20d. Reduction of the nitro compound (20d, 1 g, 2.8 mmol) is proceeded with $SnCl_2.2H_2O$ in ethanol and reflux at 80° C. for 2h, after completion of reaction ethanol is evaporated under vacuum and to this saturated sodium bicarbonate solution is added to quench the excess stannous chloride and filtered in celite bed and purified in silica column (60-120) to afforded pure compound (21d). The compound 4-(5,6,7-trimethoxybenzo[d]thiazol-2-yl)benzenamine (21d, 250 mg, 0.79 mmol) on reaction with 3,5-dimethoxybenzaldehyde (22d, 131 mg, 0.79 mmol) in ethanol using catalytic amount of acetic acid and refluxed for 2h after completion reaction mixture is cooled to 0° C. solid is precipitated from the reaction mixture it is filtered and washed with ethanol to gave the enamine product, and immediately proceeded for the next reaction with using (p-tolylsulfonyl) methyl isocyanide (tosmic) (1.5 eq), and potassium carbonate (2 eq) as base, in 10 mL of methanol and 5 mL of DME was heated under reflux for 12 h after completion of reaction as monitored by TLC. It was cooled to room temperature (27° C.); the solution was concentrated in vacuo and partitioned between EtOAc and water. The organic layer was separated, washed with brine, dried over anhydrous sodium sulfate, filtered, and concentrated in vacuo. The residue was purified by flash chromatography on silica gel eluting with EtOAc and Hexane to gave compound 7d as a brown solid (62%).

$^1$H NMR (CDCl$_3$, 400 MHz): δ 8.05 (d, 2H, J=7.6 Hz), 7.71 (s, 1H), 7.29 (d, 2H, J=7.6 Hz), 7.27 (brs, 2H), 6.29 (s, 1H), 6.24 (d, 2H, J=1.5 Hz), 4.08 (s, 3H), 3.95 (s, 3H), 3.91 (s, 3H), 3.62 (s, 6H); ESI-MS: m/z 504 [M+1]$^+$.

Example 6

4-(1-(4-(5,6,7-trimethoxybenzo[d]thiazol-2-yl)phenyl)-1H-imidazol-5-yl)benzenamine (7h)

To a stirred solution of 3,4,5-trimethoxybenzenamine (16d, 5g, 27.2 mmol) in pyridine as solvent and base to this 4-nitrobenzoyl chloride (17, 5.5g, 29.9 mmol) is added slowly and reflux for 3h, after completion of the reaction, reaction mixture is poured in water, filter and washed with dil HCl and dried to afford compound 4-nitro-N-(3,4,5-trimethoxyphenyl)benzamide (18d). To a stirred solution of amide (18d, 6g, 18.0 mmol) taken in toluene lawessons reagent (5.1g, 12.6 mmol) is added and refluxed at 110° C. for 8h. After completion of the reaction toluene is evaporated under vacuum and water is added and extracted into chloroform and finally purified by column chromatography to afford pure compound 4-nitro-N-(3,4,5-trimethoxyphenyl)benzothioamide (19d,). Treating the thioamide product (19d, 4g, 11.4 mmol) with potassium ferricyanide (4 eq) in aqueous sodium hydroxide (8 eq) solution at 90° C. for 2h cyclization takes place to obtain the 5,6,7-trimethoxy-2-(4-(4-nitrophenyl)benzo[d]thiazole (20d) solid is precipitated from the reaction mixture filtered and washed with water and dried to afforded product 20d. Reduction of the nitro compound (20d, 1 g, 2.8 mmol) is proceeded with SnCl$_2$.2H$_2$O in ethanol and reflux at 80° C. for 2h, after completion of reaction ethanol is evaporated under vacuum and to this saturated sodium bicarbonate solution is added to quench the excess stannous chloride and filtered in celite bed and purified in silica column (60-120) to afforded pure compound (21d). The compound 4-(5,6,7-trimethoxybenzo[d]thiazol-2-yl) benzenamine (21d, 250 mg, 0.79 mmol) on reaction with 4-nitrobenzaldehyde (22h, 119 mg, 1 eq) in ethanol using catalytic amount of acetic acid and refluxed for 2h after completion reaction mixture is cooled to 0° C. solid is precipitated from the reaction mixture it is filtered and washed with ethanol to gave the enamine product, and immediately proceeded for the next reaction with using (p-tolylsulfonyl) methyl isocyanide (tosmic) (1.5 eq), and potassium carbonate (2 eq) as base, in 10 mL of methanol and 5 mL of DME was heated under reflux for 12 h after completion of reaction as monitored by TLC. It was cooled to room temperature (27° C.); the solution was concentrated in vacuo and partitioned between EtOAc and water. The organic layer was separated, washed with brine, dried over anhydrous sodium sulfate, filtered, and concentrated in vacuo. The residue was purified by flash chromatography on silica gel eluting with EtOAc and Hexane to gave compound 5,6,7-trimethoxy-2-(4-(5-(4-nitrophenyl)-1H-imidazol-1-yl)phenyl)benzo[d]thiazole (25j) as a yellow solid. Reduction of (25j, 150 mg) with SnCl$_2$.2H$_2$O in ethanol reflux for 2h, after which ethanol is evaporated and quench with bicarbonate solution and extracted into ethylacetate and finally purified by column chromatography using EtOAc and Hexane to gave compound 7h as pure compound (66%).

$^1$H NMR (CDCl$_3$, 400 MHz,): δ 8.05 (d, 2H J=8.3 Hz,), 7.70 (s, 1H), 7.32 (s, 1H), 7.27 (d, 2H J=8.3 Hz), 7.15 (s, 1H), 6.94 (d, 2H, J=8.3 Hz), 6.56 (d, 2H, J=8.3 Hz), 4.10 (s, 3H), 3.96 (s, 3H), 3.94 (s, 3H); ESI-MS: m/z 459 [M+1]$^+$.

Example 7

2-methoxy-5-(1-(4-(5,6,7-trimethoxybenzo[d]thiazol-2-Ophenyl)-1H-imidazol-5-yl)benzene amine (7j)

To a stirred solution of 3,4,5-trimethoxybenzenamine (16d, 5g, 27.2 mmol) in pyridine as solvent and base 4-nitrobenzoyl chloride (17, 5.5g, 29.9 mmol) is added slowly and reflux for 2-3h, after completion of the reaction, reaction mixture is poured in water, filter and washed with dil HCl and dried to afford compound 4-nitro-N-(3,4,5-trimethoxyphenyl)benzamide (18d). To a stirred solution of amide (18d, 6g, 18.0 mmol) taken in toluene lawessons reagent (5.1g, 12.6 mmol) is added and refluxed at 110° C. for 6h. After completion of the reaction toluene is evaporated under vacuum and water is added and extracted into chloroform and finally purified by column chromatography to afford pure compound 4-nitro-N-(3,4,5-trimethoxyphenyl)benzothioamide (19d). Treating the thioamide product (19d, 4g, 11.4 mmol) with potassium ferricyanide (4 eq) in aqueous sodium hydroxide (8 eq) solution at 90° C. for 2h cyclization takes place to obtain the 5,6,7-trimethoxy-2-(4-nitrophenyl)benzo[d]thiazole (20d) solid is precipitated from the reaction mixture filtered and washed with water and dried to afforded product 20d. Reduction of the nitro compound (20d, 1 g, 2.8 mmol) is proceeded with SnCl$_2$.2H$_2$O in ethanol and reflux at 80° C. for 2h, after completion of reaction ethanol is evaporated under vacuum and to this saturated sodium bicarbonate solution is added to quench the excess stannous chloride and filtered in celite bed and purified in silica column (60-120) to afforded pure compound (21d). The compound 4-(5,6,7-trimethoxybenzo[d]thiazol-2-yl)benzenamine (21d, 250 mg, 0.79 mmol) on reaction with 4-methoxy-3-nitrobenzaldehyde (22j, 143 mg, 0.79 mmol) in ethanol using catalytic amount of acetic acid and refluxed for 2h after completion reaction mixture is cooled to 0° C. solid is precipitated from the reaction mixture it is filtered and washed with ethanol to gave the enamine product, and immediately proceeded for the next reaction by using (p-tolylsulfonyl) methyl isocyanide (tosmic) (1.5 eq), and potassium carbonate (2 eq) as base, in 10 mL of methanol and 5 mL of DME was heated under reflux for 12 h after completion of reaction as monitored by TLC. It was cooled to room temperature (27° C.); the solution was concentrated in vacuo and partitioned between EtOAc and water. The organic layer was separated, washed with brine, dried over anhydrous sodium sulfate, filtered, and concentrated in vacuo. The residue was purified by flash chromatography on silica gel eluting with EtOAc and Hexane to gave compound 5,6,7-trimethoxy-2-(4-(5-(4-methoxy-3-nitrophenyl)-1H-imidazol-1-yl) phenyl)benzo[d]thiazole 25l as a yellow solid. Reduction of (25l, 150 mg) with SnCl$_2$.2H$_2$O in ethanol reflux for 2 hr, after which ethanol is evaporated and quench with bicarbonate solution and extracted into ethylacetate and finally purified by column chromatography using EtOAc and Hexane to gave compound 7j as pure compound (63%).

$^1$H NMR (CDCl$_3$ 300 MHz,): δ 8.03 (d, 2H J=8.3 Hz), 7.75 (s, 1H), 7.32 (s, 1H), 7.27 (d, 2H, J=8.3 Hz), 7.17 (s, 1H), 6.64 (d, 1H, J=8.3), 6.55 (d, 1H, J=2.2 Hz), 6.43 (dd, 1H, J=8.3, 1.5 Hz), 4.10 (s, 3H), 3.96 (s, 3H), 3.94 (s, 3H) 3.83 (s, 3H), 3.51 (brs, 2H); ESI-MS: m/z 489 [M+1]$^+$.

Biological Activity

Some of biological activity studies were carried out at the National Cancer Institute (NCI), Maryland, USA.

Anticancer Activity:

The compounds were evaluated for anticancer activity against sixty human cancer cells derived from nine cancer types (leukemia cell line, non-small-cell lung cell line, colon cell line, CNS cell line, melanoma cell line, ovarian cell line, prostate cell line, renal cancer cell line and breast cancer cell line) as shown in Table 1. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth.

TABLE 1

The GI$_{50}$ (μM) values for compounds 3a, 3b 4c, 6d, 6e, 6f, 7d, 7h and 7j in sixty cancer cell lines.

| Cancer panel/cell line | GI$_{50}$ (μM) | | | | | | | | |
|---|---|---|---|---|---|---|---|---|---|
| | 3a | 3b | 4c | 6d | 6e | 6f | 7d | 7h | 7j |
| Leukemia | | | | | | | | | |
| CCRF-CEM | 6.45 | 0.79 | 6.92 | — | —$^a$ | 3.95 | — | — | 3.41 |
| HL-60 (TB) | 8.71 | — | 2.50 | — | 3.09 | 3.30 | 2.43 | 0.989 | 2.20 |
| K-562 | 6.02 | 36.31 | 3.93 | 3.22 | 5.88 | 3.83 | 3.57 | — | 3.38 |
| MOLT-4 | 19.50 | 26.91 | 3.41 | — | — | 4.24 | 4.11 | — | 4.00 |
| SR | 17.37 | 21.88 | 4.99 | 3.30 | 3.03 | 3.24 | 7.14 | 1.40 | 3.43 |
| RPMI-8226 | — | — | 4.11 | — | —$^a$ | 5.39 | 2.90 | — | — |
| Non-small lung | | | | | | | | | |
| A549/ATCC | 28.84 | 34.67 | 12.3 | — | 41.8 | 6.16 | 5.59 | 3.14 | 5.77 |
| EKVX | 34.67 | 4.07 | — | — | — | 5.09 | 1.87 | 2.49 | 7.54 |
| HOP-62 | —$^a$ | 30.91 | 40.7 | 6.65 | 35.5 | 75.9 | 26.4 | — | — |
| HOP-92 | — | —$^a$ | 5.47 | — | — | — | —$^a$ | 0.446 | — |
| NCI-H226 | 0.35 | 60.27 | 49.3 | 18.5 | 6.44 | — | 21.7 | 4.73 | 6.70 |
| NCI-H23 | 58.89 | 12.58 | 8.25 | 10.3 | —$^a$ | 6.15 | 9.56 | 3.87 | 4.76 |
| NCI-H322M | 43.66 | 39.82 | 36.3 | —$^a$ | —$^a$ | —$^a$ | 86.5 | 2.07 | 25.7 |
| NCI-H460 | 53.70 | 38.91 | 5.70 | 4.41 | 6.06 | 4.67 | 7.46 | 5.13 | 4.69 |
| NCI-H522 | 32.36 | 30.20 | 9.90 | 2.49 | 5.26 | 3.27 | 11.8 | 2.74 | 3.37 |
| Colon | | | | | | | | | |
| COLO 205 | 51.30 | —$^a$ | 56.8 | — | — | 4.51 | 3.85 | — | 2.94 |
| HCC-2998 | 0.25 | —$^a$ | —$^a$ | —$^a$ | —$^a$ | —$^a$ | —$^a$ | — | — |
| HCT-116 | 43.66 | 43.66 | 4.36 | 4.93 | 5.48 | 3.92 | 3.76 | 3.81 | 3.78 |
| HCT-15 | 47.86 | —$^a$ | 82.3 | — | — | 5.48 | 5.72 | — | 4.02 |
| HT29 | 29.51 | 37.16 | 10.8 | — | 7.13 | 4.88 | 8.33 | 2.79 | 3.87 |
| KM12 | —$^a$ | 57.57 | 6.40 | 4.52 | 6.80 | 4.62 | 5.54 | — | 3.80 |
| SW-620 | —$^a$ | 66.09 | 7.81 | — | —$^a$ | 5.96 | 13.7 | — | 6.21 |
| CNS | | | | | | | | | |
| SF-268 | —$^a$ | 35.48 | 12.7 | 11.3 | 9.96 | — | 22.1 | 12.3 | 47.0 |
| SF-295 | 64.59 | 31.62 | 75.9 | 2.40 | 7.00 | 4.42 | 3.64 | 1.53 | 4.44 |
| SF-539 | —$^a$ | — | —$^a$ | 5.76 | —$^a$ | 8.59 | 22.0 | 7.14 | —$^a$ |
| SNB-19 | —$^a$ | 45.72 | 20.6 | —$^a$ | —$^a$ | —$^a$ | 19.7 | 12.3 | — |
| SNB-75 | 33.12 | 15.85 | 12.6 | 3.28 | 7.21 | 6.47 | 15.0 | 5.94 | 52.3 |
| U251 | 66.09 | 31.62 | | 4.76 | 9.19 | 4.15 | 5.44 | 3.84 | 6.00 |
| Ovarian | | | | | | | | | |
| IGROV1 | 0.042 | 47.86 | 15.4 | 5.07 | 56.1 | 5.87 | 9.60 | 2.63 | 4.90 |
| OVCAR-3 | — | 38.91 | 5.71 | 2.87 | 3.85 | 3.26 | 6.07 | 2.73 | 5.18 |
| OVCAR-4 | 0.54 | 37.16 | 11.4 | — | 4.21 | 3.25 | 6.67 | 3.60 | 6.29 |
| OVCAR-5 | — | 83.19 | —$^a$ | —$^a$ | —$^a$ | —$^a$ | —$^a$ | 34.3 | —$^a$ |
| OVCAR-8 | —$^a$ | —$^a$ | 15.2 | 14.5 | 21.2 | —$^a$ | 13.4 | 4.23 | 6.19 |
| NCI/ADR-RES | — | — | 30.6 | 2.58 | —$^a$ | 5.65 | 11.0 | 1.61 | 3.12 |
| SK-OV-3 | —$^a$ | 37.16 | —$^a$ | 4.69 | —$^a$ | —$^a$ | 49.9 | 11.7 | —$^a$ |
| Renal | | | | | | | | | |
| 786-0 | —$^a$ | 29.51 | 36.1 | 7.60 | —$^a$ | 7.38 | 10.3 | 6.26 | 5.73 |
| A498 | 42.66 | 41.70 | 0.0432 | 3.15 | 2.15 | 1.83 | —$^a$ | 2.13 | 4.83 |
| ACHN | 51.30 | 53.70 | 29.1 | —$^a$ | — | 6.67 | 11.5 | 8.56 | 5.59 |
| CAKI-1 | — | 34.67 | —$^a$ | 2.13 | — | — | 3.79 | 1.41 | 4.82 |
| SN12C | 50.12 | 38.91 | 31.9 | —$^a$ | —$^a$ | —$^a$ | 31.9 | 8.95 | 9.44 |
| TK-10 | 0.18 | 77.63 | 38.8 | 16.8 | —$^a$ | 9.40 | 26.4 | 4.93 | 4.16 |
| UO-31 | 6.45 | 21.38 | 16.5 | — | 31.7 | 2.27 | 1.94 | 1.55 | 1.99 |
| RXF 393 | 70.57 | 30.20 | 13.5 | 6.58 | — | 2.80 | 30.2 | 4.41 | 5.98 |

TABLE 1-continued

The GI$_{50}$ (μM) values for compounds 3a, 3b 4c, 6d, 6e, 6f, 7d, 7h and 7j in sixty cancer cell lines.

| Cancer panel/cell line | GI$_{50}$ (μM) | | | | | | | | |
|---|---|---|---|---|---|---|---|---|---|
| | 3a | 3b | 4c | 6d | 6e | 6f | 7d | 7h | 7j |
| Prostate | | | | | | | | | |
| PC-3 | 31.62 | 50.12 | 3.47 | — | 3.66 | 2.54 | 3.17 | 3.02 | 2.59 |
| DU-145 | 61.69 | 33.88 | 14.3 | | 27.9 | —$^a$ | 31.1 | 7.25 | 6.38 |
| Breast | | | | | | | | | |
| MCF7 | 0.03 | 56.24 | 23.5 | 3.82 | 5.36 | 3.88 | 4.02 | 3.02 | 4.07 |
| MDA-MB-231/ATCC | 66.09 | 44.68 | 32.2 | 9.01 | 28.4 | 3.51 | 19.2 | 3.65 | —$^a$ |
| HS 578T | —$^a$ | 95.51 | —a | 5.02 | — | — | 20.9 | 5.36 | 28.3 |
| BT-549 | 66.09 | 14.12 | 11.5 | 3.09 | 9.12 | 5.23 | 6.71 | — | 6.21 |
| T-47D | 0.10 | 22.39 | 7.98 | 5.77 | 3.78 | 3.35 | 4.74 | 1.59 | 3.02 |
| MDA-MB-468 | | | 11.1 | 3.17 | 4.15 | 3.27 | 10.7 | 1.82 | 8.60 |
| Melanoma | | | | | | | | | |
| LOX IMVI | 37.16 | —$^a$ | 35.9 | 5.48 | —$^a$ | 5.40 | 6.93 | 3.65 | 4.75 |
| MALME-3M | —$^a$ | 83.19 | 11.1 | — | 59.8 | 3.73 | 9.58 | 0.710 | 2.48 |
| M14 | 57.57 | 33.12 | 33.4 | — | —$^a$ | 7.91 | — | 2.10 | 5.91 |
| MDA-MB-435 | 79.49 | 89.12 | 17.1 | 1.53 | — | 3.41 | 6.07 | — | 3.13 |
| SK-MEL-2 | —$^a$ | —$^a$ | 39.7 | 9.69 | 41.4 | 6.09 | 6.16 | — | 6.04 |
| SK-MEL-28 | —$^a$ | 64.59 | 35.1 | —$^a$ | —$^a$ | — | 31.6 | —$^a$ | 13.7 |
| SK-MEL-5 | 21.88 | 52.49 | 12.1 | 3.29 | 3.61 | 2.46 | 2.85 | 2.74 | 1.73 |
| UACC-257 | 74.18 | —$^a$ | 4.11 | —$^a$ | —$^a$ | —$^a$ | 20.5 | 6.40 | —$^a$ |
| UACC-62 | 70.82 | 57.57 | 8.67 | 4.75 | 8.14 | 4.14 | 13.8 | 5.45 | —$^a$ |

— not done on that cell line;
—$^a$ not active

TABLE 2

The mean graph midpoint values (MG_MID) of Log$_{10}$ GI$_{50}$ (log values of concentration in mol/L causing 50% inhibition of net cell growth) values for compounds 4c, 6d, 6e, 6f, 7d, 7h and 7j in sixty cancer cell lines.

| Cancer cell lines Log$_{10}$ GI$_{50}$ | 4c | 6d | 6e | 6f | 7d | 7h | 7j |
|---|---|---|---|---|---|---|---|
| Leukemia | −5.38 | −5.48 | −4.79 | −5.41 | −5.43 | −5.92 | −5.49 |
| Non-small cell lung | −4.83 | −4.98 | −4.64 | −4.95 | −4.82 | −5.59 | −5.18 |
| Colon | −4.71 | −4.88 | −4.60 | −5.13 | −5.04 | −5.48 | −5.40 |
| CNS | −4.52 | −5.10 | −4.72 | −4.80 | −4.92 | −5.24 | −4.53 |
| Melanoma | −4.82 | −4.98 | −4.39 | −5.18 | −5.03 | −5.32 | −5.17 |
| Ovarian | −4.62 | −5.10 | −4.53 | −4.78 | −4.79 | −5.30 | −4.93 |
| Renal | −4.98 | −4.89 | −4.60 | −5.18 | −4.83 | −5.41 | −5.31 |
| Prostate | −5.16 | >−4.0 | −4.99 | −4.79 | −5.00 | −5.33 | −5.39 |
| Breast | −4.82 | −5.34 | −5.13 | −5.42 | −5.04 | −5.55 | −4.96 |

TABLE 3

The mean graph midpoint values (MG_MID) of Log$_{10}$ LC$_{50}$ values (log value of the concentration of compounds leading to 50% net cell death) for compounds 4c, 6d, 6e, 6f, 7d, 7h and 7j in sixty cancer cell lines.

| Cancer cell lines Log$_{10}$ LC$_{50}$ | 4c | 6d | 6e | 6f | 7d | 7h | 7j |
|---|---|---|---|---|---|---|---|
| Leukemia | >−4.0 | >−4.0 | >−4.0 | >−4.0 | >−4.0 | >−4.0 | >−4.0 |
| Non-small cell lung | −4.03 | >−4.0 | >−4.0 | >−4.0 | >−4.0 | −4.03 | >−4.0 |
| Colon | >−4.0 | >−4.0 | >−4.0 | >−4.0 | >−4.0 | >−4.0 | >−4.0 |
| CNS | >−4.0 | >−4.0 | >−4.0 | >−4.0 | >−4.0 | −4.18 | >−4.0 |
| Melanoma | >−4.0 | >−4.0 | >−4.0 | >−4.0 | >−4.0 | −4.01 | −4.09 |
| Ovarian | >−4.0 | >−4.0 | >−4.0 | >−4.0 | >−4.0 | −4.05 | >−4.0 |
| Renal | −4.02 | >−4.0 | >−4.0 | >−4.0 | >−4.0 | −4.02 | >−4.0 |
| Prostate | >−4.0 | >−4.0 | >−4.0 | >−4.0 | >−4.0 | >−4.0 | >−4.0 |
| Breast | >−4.0 | >−4.0 | >−4.0 | >−4.0 | >−4.0 | >−4.0 | >−4.0 |

TABLE 4

The mean graph midpoint values (MG_MID) of log$_{10}$ TGI (log value of concentration of the compound resulting in total inhibition of net cell growth) for compounds 4c, 6d, 6e, 6f, 7d, 7h and 7j in sixty cancer cell lines.

| Cancer cell lines Log$_{10}$ TGI | 4c | 6d | 6e | 6f | 7d | 7h | 7j |
|---|---|---|---|---|---|---|---|
| Leukemia | −4.19 | >−4.0 | >−4.0 | >−4.0 | >−4.0 | >−4.0 | −4.20 |
| Non-small cell lung | 4.41 | −4.05 | −4.01 | >−4.0 | >−4.0 | −4.54 | −4.11 |
| Colon | −4.06 | >−4.0 | >−4.0 | >−4.0 | >−4.0 | >−4.0 | −4.11 |
| CNS | −4.05 | −4.19 | −4.06 | >−4.0 | −4.11 | −4.51 | >−4.0 |
| Melanoma | >−4.0 | >−4.0 | >−4.0 | >−4.0 | −4.02 | −4.13 | −4.26 |
| Ovarian | −4.11 | >−4.0 | >−4.0 | >−4.0 | −4.08 | −4.56 | >−4.0 |
| Renal | −4.11 | >−4.0 | >−4.0 | >−4.0 | −4.03 | −4.38 | −4.14 |
| Prostate | −4.06 | >−4.0 | >−4.0 | >−4.0 | >−4.0 | −4.15 | >−4.0 |
| Breast | −4.02 | >−4.0 | >−4.0 | >−4.0 | >−4.0 | −4.47 | >−4.0 |

TABLE 5

Comparative data of present compounds (7h, 7j, 7d and 4c) with previous compounds (3c and 3d; U.S. Pat. No. 7,384,966)

| Cancer panel/cell line | Log$_{10}$GI$_{50}$(μM) | | | | | |
|---|---|---|---|---|---|---|
| | 3c | 3d | 7h | 7j | 7d | 4c |
| Leukemia | | | | | | |
| CCRF-CEM | −4.06 | >−4.0 | | −5.47 | — | −5.16 |
| HL-60(TB) | | >−4.0 | −6.00 | −5.66 | −5.61 | −5.60 |

TABLE 5-continued

Comparative data of present compounds (7h, 7j, 7d and 4c) with previous compounds (3c and 3d; U.S. Pat. No. 7,384,966)

| Cancer panel/cell line | Log₁₀GI₅₀(μM) | | | | | |
|---|---|---|---|---|---|---|
| | 3c | 3d | 7h | 7j | 7d | 4c |
| K-562 | >−4.0 | >−4.0 | | −5.47 | −5.45 | −5.41 |
| MOLT | −4.03 | >−4.0 | | −5.40 | −5.39 | −5.47 |
| Non-small lung | | | | | | |
| A549/ATCC | −4.97 | >−4.0 | −5.50 | −5.24 | −5.25 | −4.91 |
| EKVX | −5.67 | >−4.0 | −5.60 | −5.12 | −5.73 | — |
| HOP-62 | — | >−4.0 | — | — | −4.58 | −4.39 |
| HOP-92 | — | — | −6.35 | — | >−4.0 | −5.26 |
| NCI-H23 | −4.95 | >−4.0 | −5.41 | −5.32 | −5.02 | −5.08 |
| NCI-H522 | −4.87 | >−4.0 | −5.56 | −5.47 | −4.93 | −5.00 |
| Colon | | | | | | |
| SW-620 | >−4.0 | >−4.0 | — | −5.21 | −4.86 | −5.11 |
| CNS | | | | | | |
| SF-268 | −4.30 | >−4.0 | −4.91 | −4.33 | −4.66 | −4.51 |
| SF-295 | −4.50 | >−4.0 | −5.82 | −5.35 | −5.44 | −4.90 |
| SF-539 | >−4.0 | >−4.0 | −5.15 | >−4.0 | −4.66 | −4.12 |
| SNB-19 | >−4.0 | >−4.0 | −4.91 | >−4.0 | −4.70 | >−4.0 |
| SNB-75 | — | >−4.0 | −5.23 | −4.28 | −4.82 | −4.69 |
| U251 | −4.15 | >−4.0 | −5.42 | −5.22 | −5.26 | −4.90 |
| Ovarian | | | | | | |
| OVCAR-3 | −5.37 | >−4.0 | −5.56 | −5.29 | −5.22 | −5.24 |
| OVCAR-8 | >−4.0 | >−4.0 | −5.37 | −5.21 | −4.87 | −4.82 |
| NCI/ADR-RES | — | — | −5.79 | −5.51 | −4.96 | −4.51 |
| SK-OV-3 | −4.78 | >−4.0 | −4.93 | >−4.0 | −4.30 | >−4.0 |
| Renal | | | | | | |
| 786-0 | −4.60 | >−4.0 | −5.20 | −5.24 | −4.99 | −4.44 |
| A498 | −5.01 | — | −5.67 | −5.32 | >−4.0 | −7.36 |
| ACHN | −5.17 | >−4.0 | −5.07 | −5.25 | −4.94 | −4.54 |
| CAKI-1 | −4.63 | >−4.0 | −5.85 | −5.32 | −5.42 | — |
| SN12C | >−4.0 | >−4.0 | −5.05 | −5.03 | −4.50 | −4.50 |
| UO-31 | >−4.0 | >−4.0 | −5.81 | −5.70 | −5.71 | −4.78 |
| RXF 393 | — | — | −5.36 | −5.22 | −4.52 | −4.87 |
| Prostate | | | | | | |
| PC-3 | >−4.0 | >−4.0 | −5.52 | −5.59 | −5.50 | −5.46 |
| DU-145 | −4.06 | >−4.0 | −5.04 | −5.20 | −4.51 | −4.85 |
| Breast | | | | | | |
| MDA-MB-231/ATCC | −4.26 | >−4.0 | −5.44 | >−4.0 | −4.72 | −4.49 |
| HS 578T | — | >−4.0 | −5.27 | −4.55 | −4.68 | — |
| BT-549 | −4.77 | >−4.0 | — | −5.21 | −5.17 | −4.94 |
| MDA-MB-468 | — | — | −5.74 | −5.07 | −4.97 | −4.96 |
| Melanoma | | | | | | |
| LOX IMVI | −4.19 | >−4.0 | −5.44 | −5.32 | −5.16 | −4.44 |
| MALME-3M | >−4.0 | >−4.0 | −6.15 | −5.61 | −5.02 | −4.95 |
| M14 | >−4.0 | >−4.0 | −5.68 | −5.23 | — | −4.48 |
| MDA-MB-435 | — | — | — | −5.50 | −5.22 | −4.77 |
| SK-MEL-2 | — | — | — | −5.22 | −5.21 | −4.40 |
| SK-MEL-28 | — | — | >−4.0 | −4.86 | −4.50 | −4.45 |
| UACC-257 | >−4.0 | >−4.0 | −5.19 | >−4.0 | −4.69 | −5.39 |
| UACC-62 | −4.37 | >−4.0 | −5.26 | −5.04 | −4.86 | −5.06 |

Effect of Compounds on Cell Cycle Distribution.

Figure 1:
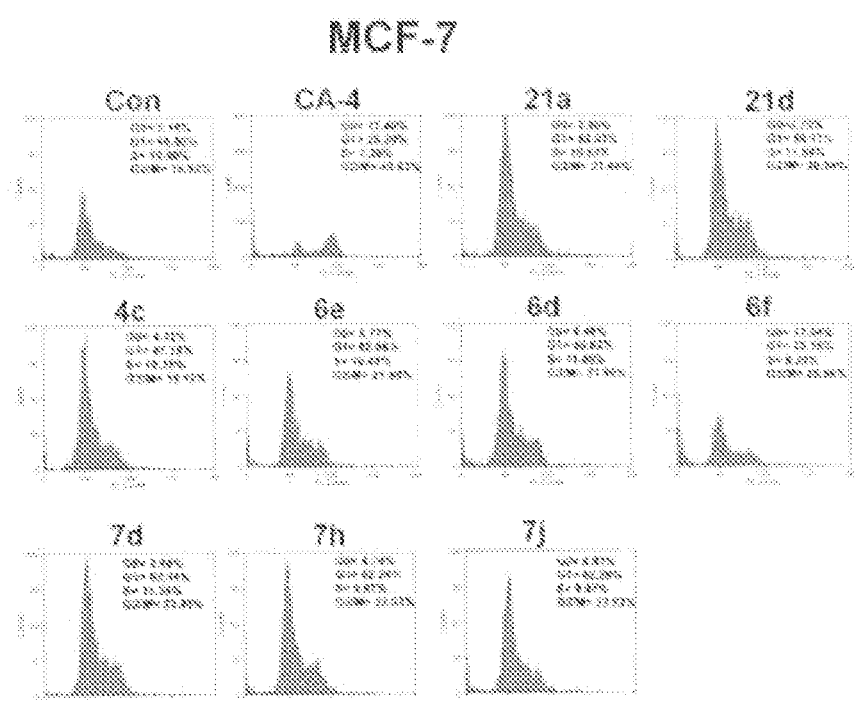
FIG. 1 represents FACS analysis of cell cycle distribution of MCF-7 cells after treatment with compounds CA-4, 21a, 21d, 4c, 6d, 6e, 6f, 7d, 7h and 7j at 2 μM concentration for 24h and control cells are the cells treated with DMSO (0.25%).

In order to investigate the mechanism underlying the antiproliferative effect of the compounds the cell cycle distribution was analyzed in K562 (Leukemia) and MCF-7 (Breast carcinoma) cell lines by flow cytometry. Compounds CA-4, 21a, 21d, 4c, 6d, 6e, 6f, 7d, 7h and 7j have shown 1.72%, 14%, 12%, 14%, 12%, 14%, 14%, 16%, 16% &12% in K562 cells and 49.63%, 21%, 20%, 18%, 21%, 21%, 21%, 24%, 23% and 23% in MCF-7 cell line respectively. Compound 7d treated cells showed highest G2/M phase with 16 and 24% of cells in K562 and MCF-7 cells. Thus compound 7d was considered for further studies (FIG. 1).

Effect of Compound 7d on the Inhibition of Tubulin Polymerization Activity

Figure 2:
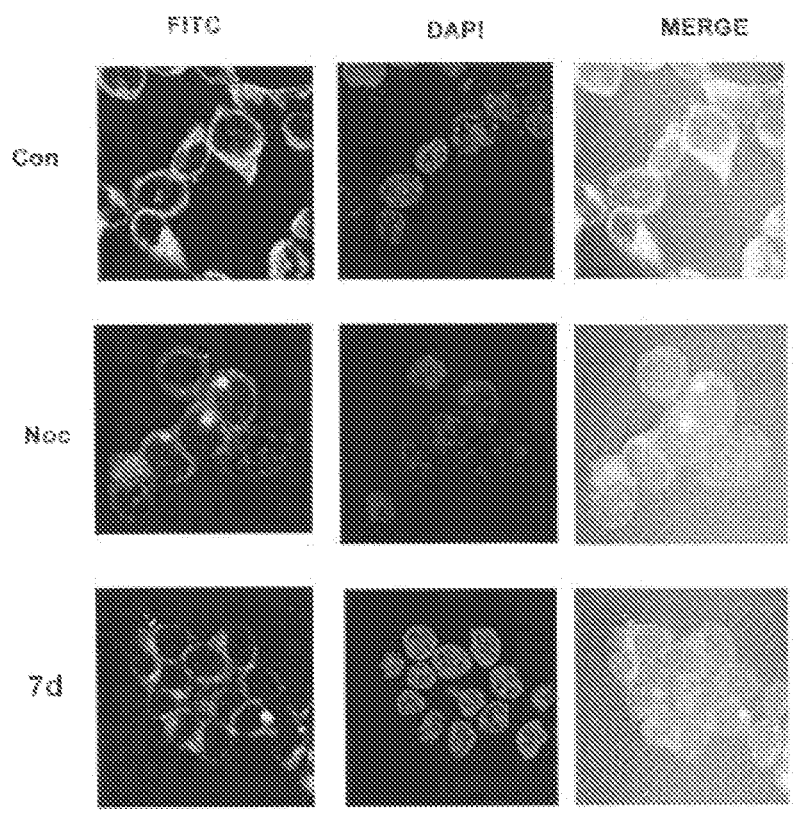
FIG. 2 represents effect of compound 7d, the effective compound on the microtubule network of MCF-7 cells untreated cells (Con), nocodazole (Noc) and 7d at 2 μM concentration. Microtubules and unassembled tubulin are shown in green and DNA was stained with nuclear dye DAPI (4,6-diamidino-2-phenylindole) is shown in blue colour.

Inhibition of tubulin is associated with G2/M cell cycle arrest by interrupting chromosome segregation and affecting mitotic spindle formation. Since 7d is the most effective compound in causing G2/M cell cycle arrest in both the cell lines tested. It was considered of interest to understand the mechanism of anti-cancer activity of compound 7d with regard to interaction with microtubule system. MCF-7 breast cancer cells were treated with Nocodazole (Noc), 7d compounds at 2 μM concentration. We observed disrupted microtubulin organization in Nocadazole and 7d compound treated cells (FIG. 2).

Effect of Compounds on Apoptosis.

Figure 3:
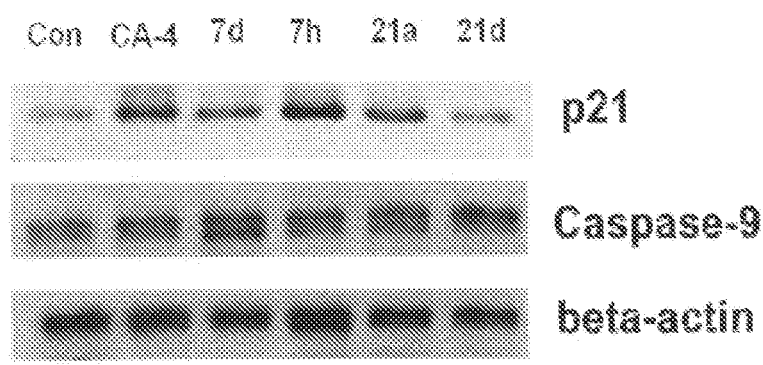
FIG. 3 represents effect of compound 7d and 7h on p21 and caspase-9. MCF-7 cells were treated with 2 μM concentration of compounds 7d and 7h for 24h. The cell lysates were collected and probed with anti-bodies against p21 and caspase-9. beta-actin was used as loading control. Con: Control (untreated).

Activation of tumor suppressor gene p21 was the important regulator of apoptotic pathway caused by various stimuli. In many instances the apoptotic cell death is mediated by caspases, thus the possible involvement of p21 and caspase protein and its role in apoptosis has been investigated. MCF-7 cells were treated with 7d, 7h (the effective compounds of cell cycle arrest) 21a, 21d and CA-4 at 2 μM concentration. Western blot analysis revealed that treatment of MCF-7 cells with compounds caused increase in p21 and caspase-9 protein (FIG. 3).

Advantages of the Present Invention

1. The present invention provides 2-phenyl benzothiazole linked imidazole compounds of general formula A.
2. It also provides a process for the preparation of 2-phenyl benzothiazole linked imidazole compounds of general formula A.

The invention claimed is:

1. A compound of formula A

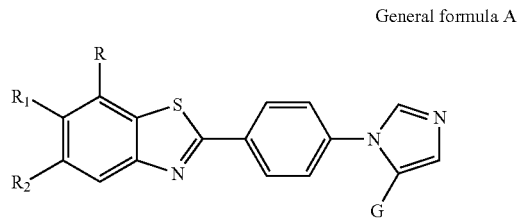

General formula A wherein

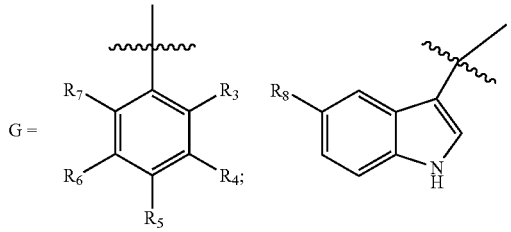

-continued

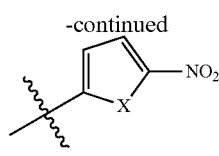

X = NH, S

R = H or OCH₃;
R₁ = H, F or OCH₃;
R₂ = H or OCH₃;
R₃ = H, NH₂, F or OCH₃;
R₄ = H, NH₂ or OCH₃;
R₅ = H, NH₂, F, CF₃ or OCH₃;
R₆ = H or OCH₃;
R₇ = H or OCH₃;
R₈ = H or OCH₃.

2. A compound of formula A as claimed in claim 1 selected from the group consisting of:
6-Fluoro-2-(4-(5-phenyl-1H-imidazol-1-yl)phenyl)benzo[d]thiazole (4a);
6-Fluoro-2-(4-(5-(4-(trifluoromethyl)phenyl)-1H-imidazol-1yl)phenyl)benzo[d]thiazole (4b);
6-Fluoro-2-(4-(5-(4-fluoro-3-methoxyphenyl)-1H-imidazol-1-yl)phenyl)benzo[d] thiazole (4c);
2-(4-(5-(3,5-Dimethoxyphenyl)-1H-imidazol-1-yl)phenyl)-6-fluorobenzo[d]thiazole (4d);
2-(4-(5-(3,4-Dimethoxyphenyl)-1H-imidazol-1-yl)phenyl)-6-fluorobenzo[d]thiazole (4e);
6-Fluoro-2-(4-(5-(3,4,5-trimethoxyphenyl)-1H-imidazol-1-yl)phenyl)benzo[d]thiazole (4f);
6-Fluoro-2-(4-(5-(2,4,6-trimethoxyphenyl)-1H-imidazol-1-yl)phenyl)benzo[d]thiazole (4g);
4-(1-(4-(6-Fluorobenzo[d]thiazol-2-yl)phenyl)-1H-imidazol-5-yl)benzenamine (4h);
2-(1-(4-(6-Fluorobenzo[d]thiazol-2-yl)phenyl)-1H-imidazol-5-yl)-5-methoxybenzene amine (4i)
5-(1-(4-(6-Fluorobenzo[d]thiazol-2-yl)phenyl)-1H-imidazol-5-yl)-2-methoxy benzenamine (4j);
6-Methoxy-2-(4-(5-phenyl-1H-imidazol-1-yl)phenyl)benzo[d]thiazole (5a);
6-Methoxy-2-(4-(5-(4-(trifluoromethyl)phenyl)-1H-imidazol-1-yl)phenyl)benzo[d]thiazole (5b);
2-(4-(5-(4-Fluoro-3-methoxyphenyl)-1H-imidazol-1-yOphenyl)-6-methoxybenzo[d] thiazole (5c);
2-(4-(5-(3,5-Dimethoxyphenyl)-1H-imidazol-1-yl)phenyl)-6-methoxybenzo[d]thiazole (5d);
2-(4-(5-(3,4-Dimethoxyphenyl)-1H-imidazol-1-yl)phenyl)-6-methoxybenzo[d]thiazole (5e);
6-Methoxy-2-(4-(5-(3,4,5-trimethoxyphenyl)-1H-imidazol-1-yl)phenyl)benzo[d]thiazole (5f);
6-Methoxy-2-(4-(5-(2,4,6-trimethoxyphenyl)-1H-imidazol-1-yl)phenyl)benzo[d]thiazole (5g);
4-(1-(4-(6-Methoxybenzo[d]thiazol-2-yl)phenyl)-1H-imidazol-5-yl)benzenamine (5h);
5-Methoxy-2-(1-(4-(6-methoxybenzo[d]thiazol-2-yl)phenyl)-1H-imidazol-5-yl)benzene amine (5i);
2-Methoxy-5-(1-(4-(6-methoxybenzo[d]thiazol-2-yl)phenyl)-1H-imidazol-5-yl)benzene amine (5j);
5,7-Dimethoxy-2-(4-(5-phenyl-1H-imidazol-1-yl)phenyl)benzo[d]thiazole (6a);
5,7-Dimethoxy-2-(4-(5-(4-(trifluoromethyl)phenyl)-1H-imidazol-1-yl)phenyl)benzo[d] thiazole (6b);
2-(4-(5-(4-Fluoro-3-methoxyphenyl)-1H-imidazol-1-yl)phenyl)-5,7-dimethoxybenzo[d] thiazole (6c)
2-(4-(5-(3,5-Dimethoxyphenyl)-1H-imidazol-1-yl)phenyl)-5,7-dimethoxybenzo[d] thiazole (6d);
2-(4-(5-(3,4-Dimethoxyphenyl)-1H-imidazol-1-yl)phenyl)-5,7-dimethoxybenzo[d] thiazole (6e),
5,7-Dimethoxy-2-(4-(5-(3,4,5-trimethoxyphenyl)-1H-imidazol-1-yl)phenyl)benzo[d] thiazole (6f);
5,7-Dimethoxy-2-(4-(5-(2,4,6-trimethoxyphenyl)-1H-imidazol-1-yl)phenyl)benzo[d] thiazole (6g);
4-(1-(4-(5,7-Dimethoxybenzo[d]thiazol-2-yl)phenyl)-1H-imidazol-5-yl)benzenamine (6h);
2-(1-(4-(5,7-Dimethoxybenzo[d]thiazol-2-yl)phenyl)-1H-imidazol-5-yl)-5-methoxy benzenamine (6i);
5-(1-(4-(5,7-Dimethoxybenzo[d]thiazol-2-yl)phenyl)-1H-imidazol-5-yl)-2-methoxy benzenamine (6j);
5,6,7-Trimethoxy-2-(4-(5-phenyl-1H-imidazol-1-yl)phenyl)benzo[d]thiazole (7a);
5,6,7-Trimethoxy-2-(4-(5-(4-(trifluoromethyl)phenyl)-1H-imidazol-1-yl)phenyl)benzo[d] thiazole (7b);
2-(4-(5-(4-Fluoro-3-methoxyphenyl)-1H-imidazol-1-yl)phenyl)-5,6,7-trimethoxybenzo[d]thiazole (7c);
2-(4-(5-(3,5-Dimethoxyphenyl)-1H-imidazol-1-yl)phenyl)-5,6,7-trimethoxybenzo[d] thiazole (7d);
2-(4-(5-(3,4-Dimethoxyphenyl)-1H-imidazol-1-yl)phenyl)-5,6,7-trimethoxybenzo[d] thiazole (7e);
5,6,7-Trimethoxy-2-(4-(5-(3,4,5-trimethoxyphenyl)-1H-imidazol-1-yl)phenyl)benzo[d] thiazole (7f);
5,6,7-Trimethoxy-2-(4-(5-(2,4,6-trimethoxyphenyl)-1H-imidazol-1-yl)phenyl)benzo[d] thiazole (7g);
4-(1-(4-(5,6,7-Trimethoxybenzo[d]thiazol-2-yl)phenyl)-1H-imidazol-5-yl)benzenamine (7h);
2-(1-(4-(5,7-Dimethoxybenzo[d]thiazol-2-yl)phenyl)-1H-imidazol-5-yl)-5-methoxy benzenamine (7i);
2-Methoxy-5-(1-(4-(5,6,7-trimethoxybenzo[d]thiazol-2-yl)phenyl)-1H-imidazol-5-yl) benzeneamine (7j);
2-(4-(5-(1H-Indol-3-yl)-1H-imidazol-1-yl)phenyl)-6-fluorobenzo[d]thiazole (8a);
6-Fluoro-2-(4-(5-(5-methoxy-1H-indol-3-yl)-1H-imidazol-1-yl)phenyl)benzo[d]thiazole (8b);
2-(4-(5-(1H-Indol-3-yl)-1H-imidazol-1-yl)phenyl)-6-methoxybenzo[d]thiazole (9a);
6-Methoxy-2-(4-(5-(5-methoxy-1H-indol-3-yl)-1H-imidazol-1-yl)phenyl)benzo[d] thiazole (9b);
2-(4-(5-(1H-Indol-3-yl)-1H-imidazol-1-yl)phenyl)-5,7-dimethoxybenzo[d]thiazole (10a);
5,7-Dimethoxy-2-(4-(5-(5-methoxy-1H-indol-3-yl)-1H-imidazol-1-yl)phenyl)benzo[d] thiazole (10b);
2-(4-(5-(1H-Indol-3-yl)-1H-imidazol-1-yl)phenyl)-5,6,7-trimethoxybenzo[d]thiazole (11a);
5,6,7-Trimethoxy-2-(4-(5-(5-methoxy-1H-indol-3-yl)-1H-imidazol-1-yl)phenyl)benzo[d] thiazole (11b);
6-Fluoro-2-(4-(5-(5-nitro-1H-pyrrol-2-yl)-1H-imidazol-1-yl)phenyl)benzo[d]thiazole (12a);
6-Fluoro-2-(4-(5-(5-nitrothiophen-2-yl)-1H-imidazol-1-yl)phenyl)benzo[d]thiazole (12b);
6-Methoxy-2-(4-(5-(5-nitro-1H-pyrrol-2-yl)-1H-imidazol-1-yl)phenyl)benzo[d]thiazole (13a),
6-Methoxy-2-(4-(5-(5-nitrothiophen-2-yl)-1H-imidazol-1-yl)phenyl)benzo[d]thiazole (13b);
5,7-Dimethoxy-2-(4-(5-(5-nitro-1H-pyrrol-2-yl)-1H-imidazol-1-yl)phenyl)benzo[d] thiazole (14a);
5,7-Dimethoxy-2-(4-(5-(5-nitrothiophen-2-yl)-1H-imidazol-1-yl)phenyl)benzo[d]thiazole (14b);
5,6,7-Trimethoxy-2-(4-(5-(5-nitro-1H-pyrrol-2-yl)-1H-imidazol-1-yl)phenyl)benzo[d] thiazole (15a); and
5,6,7-Trimethoxy-2-(4-(5-(5-nitrothiophen-2-yl)-1H-imidazol-1-yl)phenyl)benzo[d]thiazole (15b).

3. A compound of formula 4c, 6d, 6e, 6f, 7d, 7h or 7j as claimed in claim 2, wherein said compound exhibits in vitro anticancer activity against sixty human cancer cell lines, derived from nine cancer cell types selected from the group consisting of: leukemia cell line, non-small cell lung cell line, colon cell line, CNS cell line, renal cell line, prostate cell line, ovarian cell line, breast and melanoma cell line.

4. A compound of formula 4c, 6d, 6e, 6f, 7d, 7h or 7j as claimed in claim 2, wherein said compound exhibits in vitro anticancer activity against a leukemia cancer cell line selected from the group consisting of: CCRF-CEM, HL-60, K-562, MOLT-4, and SR, RPMI-8226, for $GI_{50}$ in the range of 2.50 to 6.92, 3.22 to 3.30, 3.03 to 5.88, 3.24 to 5.39, 2.43 to 7.14, 0.989 to 1.40, and 2.20 to 4.00 μM, respectively, at an exposure period of at least 48 hr.

5. A compound of formula 4c, 6d, 6e, 6f, 7d, 7h or 7j as claimed in claim 2, wherein said compound exhibits in vitro anticancer activity against a non-small cell lung cancer cell line selected from the group consisting of: A549/ATCC, EKVX, HOP-62, HOP-92, NCI-H226, NCI-H23, NCI-H322M, NCI-H460, and NCI-H522, for $GI_{50}$ in the range of 5.47 to 49.3, 2.49 to 18.5, 5.26 to 41.8, 3.27 to 75.9, 1.87 to 86.5, 0.446 to 5.13, and 3.37 to 25.7 μM, respectively, at an exposure period of at least 48 hr.

6. A compound of formula 4c, 6d, 6e, 6f, 7d, 7h or 7j as claimed in claim 2, wherein said compound exhibits in vitro anticancer activity against a colon cancer cell line selected from the group consisting of: COLO 205, HCC-2998, HCT-116, HCT-15, HT29, KM12, and SW-620, for $GI_{50}$ in the range of 4.36 to 82.3, 4.52 to 4.93, 5.48 to 7.13, 3.92 to 5.96, 3.76 to 13.7, 2.79 to 3.81, and 2.94 to 6.21 μM, respectively, at an exposure period of at least 48 hr.

7. A compounds of formula 4c, 6d, 6e, 6f, 7d, 7h or 7j as claimed in claim 2, wherein said compound exhibits in vitro anticancer activity against a CNS cancer cell line selected from the group consisting of: SF-268, SF-295, SF-539, SNB-19, SNB-75, and U251, for $GI_{50}$ in the range of 12.6 to 75.9, 2.40 to 11.3, 7.00 to 9.96, 4.15 to 8.59, 3.64 to 22.1, 1.53 to 12.3, and 4.44 to 52.3 μM, respectively, at an exposure period of at least 48 hr.

8. A compound of formula 4c, 6d, 6e, 6f, 7d, 7h or 7j as claimed in claim 2, wherein said compound exhibits in vitro anticancer activity against a renal cancer cell line selected from the group consisting of: 786-0, A498, ACHN, CAKI-1, SN12C, TK-10 UO-31, and RXF 393, for $GI_{50}$ in the range of 0.0432 to 38.8, 2.13 to 16.8, 2.15 to 3.17, 1.83 to 9.40, 1.94 to 31.9, 1.41 to 8.95, and 1.99 to 9.44 μM, respectively, at an exposure period of at least 48 hr.

9. A compound of formula 4c, 6e, 6f, 7d, 7h or 7j as claimed in claim 2, wherein said compound exhibits in vitro anticancer activity against a prostate cancer cell line selected from the group consisting of: PC-3, and DU-145, for $GI_{50}$ in the range of 3.47 to 14.3, 3.66 to 27.9, 2.54, 3.17 to 31.1, 3.02 to 7.25, and 2.59 to 6.38 μM, respectively, at an exposure period of at least 48 hr.

10. A compound of formula 4c, 6d, 6e, 6f, 7d, 7h or 7j as claimed in claim 2, wherein said compound exhibits in vitro anticancer activity against an ovarian cancer cell line selected from the group consisting of: IGROV1, OVCAR-3, OVCAR-4, OVCAR-5, OVCAR-8, NCI/ADR-RES, and SK-OV-3, for $GI_{50}$ in the range of 5.71 to 30.6, 2.87 to 14.5, 3.85 to 56.1, 3.25 to 5.87, 6.07 to 49.9, 1.61 to 34.3, and 3.12 to 6.29 μM, respectively, at an exposure period of at least 48 hr.

11. A compound of formula 4c, 6d, 6e, 6f, 7d, 7h or 7j as claimed in claim 2, wherein said compound exhibits in vitro anticancer activity against a breast cancer cell line selected from the group consisting of: MCF7, MDA-MB-231/ATCC, HS 578T, BT-549, TD-47D, and MDA-MB-468, for $GI_{50}$ in the range of 7.98 to 32.2, 3.09 to 9.01, 3.78 to 28.4, 3.27 to 5.23, 4.02 to 20.9, 1.59 to 5.36, and 3.02 to 28.3 μM, respectively, at an exposure period of at least 48 hr.

12. A compound of formula 4c, 6d, 6e, 6f, 7d, 7h or 7j as claimed in claim 2, wherein said compound exhibits in vitro anticancer activity against a melanoma cancer cell line selected from the group consisting of: LOX IMVI, MALME-3M, M14, MDA-MB-435, SK-MEL-2, SK-MEL-28, SK-MEL-5, UACC-257, and UACC-62 for $GI_{50}$ in the range of 4.11 to 39.7, 1.53 to 9.69, 3.61 to 59.8, 2.46 to 7.91, 2.85 to 31.6, 0.710 to 6.40, and 1.73 to 13.7 μM, respectively, at an exposure period of at least 48 hr.

13. A compound of formula 4c, 6d, 6e, 6f, 7d, 7h or 7j as claimed in claim 2, wherein said compound exhibits mean graph midpoint values (MG_MID) of $\log_{10}GI_{50}$ to a cancer cell line selected from the group consisting of: leukemia cell line, non-small cell lung cell line, colon cell line, CNS cell line, renal cell line, prostate cell line, ovarian cell line, breast and melanoma cell line in the range of −5.38 to −4.52, −5.48 to −4.0, −5.13 to −4.39, −5.42 to −4.78, −5.43 to −4.82, −5.92 to −5.24 and −5.49 to −4.53, respectively, at an exposure period of at least 48 h.

14. A compound of formula 4c, 6d, 6e, 6f, 7d, 7h or 7j as claimed in claim 2, wherein said compounds exhibiting mean graph midpoint values (MG_MID) of $\log_{10}LC_{50}$ to nine cancer cell lines (leukemia cell line, non-small cell lung cell line, colon cell line, CNS cell line, renal cell line, prostate cell line, ovarian cell line, breast and melanoma cell line) in the range of −4.00 to −4.03, −4.00, −4.00, −4.00, −4.00 to −4.18, −4.00 to −4.09, −4.00, respectively, at an exposure period of at least 48 h.

15. A compound of formula 4c, 6d, 6e, 6f, 7d, 7h or 7j as claimed in claim 2, wherein said compounds exhibiting mean graph midpoint values (MG_MID) of $\log_{10}TGI$ to nine cancer cell lines (leukemia cell line, non-small cell lung cell line, colon cell line, CNS cell line, renal cell line, prostate cell line, ovarian cell line, breast and melanoma cell line) in the range of −4.00 to −4.41, −4.00 to −4.19, −4.00 to −4.06, −4.00, −4.00 to −4.54, −4.00 to −4.26 and −4.00 to −4.11, respectively, at an exposure period of at least 48 h.

16. A process for the preparation of 2-phenyl benzothiazole linked imidazole compounds of formula A as claimed in claim 1, the said process comprising:
  i. adding 4-nitrobenzoyl chloride (17) (1.1 eq.) to a stirred solution of substituted anilines (16a-d)(1 eq.) in pyridine and reflux for period in the range of 2 to 3h to obtain coupled amide of formula 18a-d;

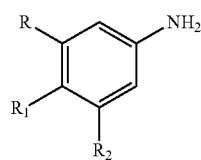

R = hydrogen or methoxy;
$R_1$ = hydrogen, methoxy or fluoro;
$R_2$ = hydrogen or methoxy;

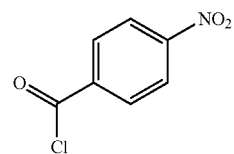

-continued

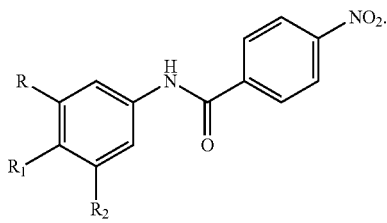

18a-d

R = hydrogen or methoxy;
R₁ = hydrogen, methoxy or fluoro;
R₂ = hydrogen or methoxy ii. treating the amide of formula (18a-d) as obtained in step (i) with Lawesson's reagent, in toluene under reflux conditions for 6 to 8 hr. at 110° C., to obtain the corresponding thioamides (19a-d);

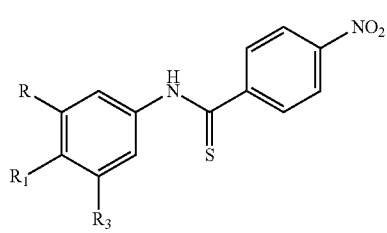

19a-d iii. treating the thioamides (19a-d)(1 eq.) as obtained in step (ii) with potassium ferricyanide (4 eq.) in aqueous sodium hydroxide solution at 90° C. for 2 to 3 hr. to obtain the substituted 2-(4-nitro phenyl benzothiazole) of formula 20a-d;

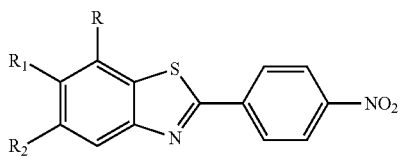

20a-d iv. reducing the substituted 2-(4-nitro phenyl benzothiazole) of formula 20a-d with $SnCl_2.2H_2O$ to obtain amine compounds (21a-d);

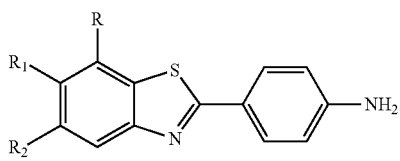

21a-d v. treating the amine compounds (21a-d) as obtained in step (iv) with substituted aldehydes in the presence of catalytic amount of 2 to 3 drops of acetic acid in ethanol solution reflux at 80° C. to obtain an imine compound followed by treatment with p-toulenesulfonyl methyl isocyanide and potassium carbonate to obtain a nitro intermediate of formula (25a-l) and a compound of formula 4a-g to 7a-g and 8a-b to 15a-b having the formulae 6-Fluoro-2-(4-(5-phenyl-1H-imidazol-1-yl) phenyl) benzo[d]thiazole (4a); 6-Fluoro-2-(4-(5-(4-(trifluoromethyl)phenyl)-1H-imidazol-1yl)phenyl)benzo[d]thiazole (4b); 6-Fluoro-2-(4-(5-(4-fluoro-3-methoxyphenyl)-1H-imidazol-1-yl)phenyl)benzo[d] thiazole (4c); 2-(4-(5-(3,5-Dimethoxyphenyl)-1H-imidazol-1-yl) phenyl)-6-fluorobenzo[d]thiazole (4d); 2-(4-(5-(3,4-Dimethoxyphenyl)-1H-imidazol-1-yl)phenyl)-6-fluorobenzo[d]thiazole (4e); 6-Fluoro-2-(4-(5-(3,4,5-trimethoxyphenyl)-1H-imidazol-1-yl)phenyl)benzo[d] thiazole (4f); 6-Fluoro-2-(4-(5-(2,4,6-trimethoxyphenyl)-1H-imidazol-1-yl)phenyl)benzo[d] thiazole (4g); 5,6,7-Trimethoxy-2-(4-(5-phenyl-1H-imidazol-1-yl)phenyl)benzo[d]thiazole (7a); 5,6,7-Trimethoxy-2-(4-(5-(4-(trifluoromethyl)phenyl)-1H-imidazol-1-yl)phenyl)benzo[d] thiazole (7b); 2-(4-(5-(4-Fluoro-3-methoxyphenyl)-1H-imidazol-1-yl) phenyl)-5,6,7-trimethoxybenzo [d]thiazole (7c); 2-(4-(5-(3,5-Dimethoxyphenyl)-1H-imidazol-1-yl)phenyl)-5,6,7-trimethoxybenzo[d] thiazole (7d); 2-(4-(5-(3,4-Dimethoxyphenyl)-1H-imidazol-1-yl)phenyl)-5,6,7-trimethoxybenzo[d] thiazole (7e); 5,6,7-Trimethoxy-2-(4-(5-(3,4,5-trimethoxyphenyl)-1H-imidazol-1-yl) phenyl)benzo[d] thiazole (7f); 5,6,7-Trimethoxy-2-(4-(5-(2,4,6-trimethoxyphenyl)-1H-imidazol-1-yl)phenyl) benzo[d] thiazole (7g); 4-(1-(4-(5,6,7-Trimethoxybenzo[d]thiazol-2-yl)phenyl)-1H-imidazol-5-yl)benzenamine (7h); 2-(1-(4-(5,7-Dimethoxybenzo [d]thiazol-2-yl)phenyl)-1H-imidazol-5-yl)-5-methoxy benzenamine (7i); 2-Methoxy-5-(1-(4-(5,6,7-trimethoxybenzo[d]thiazol-2-yl)phenyl)-1H-imidazol-5-yl) benzeneamine (7j); 2-(4-(5-(1H-Indol-3-yl)-1H-imidazol-1-yl)phenyl)-6-fluorobenzo[d]thiazole (8a); 6-Fluoro-2-(4-(5-(5-methoxy-1H-indol-3-yl)-1H-imidazol-1-yl)phenyl)benzo[d]thiazole (8b); 5,6,7-Trimethoxy-2-(4-(5-(5-nitro-1H-pyrrol-2-yl)-1H-imidazol-1-yl)phenyl)benzo[d] thiazole (15a); and 5,6,7-Trimethoxy-2-(4-(5-(5-nitrothiophen-2-yl)-1H-imidazol-1-yl)phenyl)benzo[d]thiazole (15b);

vi. reducing the nitro intermediate 25a-l as obtained in step (v) with $SnCl_2.2H_2O$ in ethanol to obtain the compound of formula 4h-j to 7h-j, wherein 4h-j have the formula 4-(1-(4-(6-Fluorobenzo[d]thiazol-2-yl)phenyl)-1H-imidazol-5-yl)benzenamine (4h); 2-(1-(4-(6-Fluorobenzo[d]thiazol-2-yl)phenyl)-1H-imidazol-5-yl)-5-methoxybenzeneamine (4i); and 5-(1-(4-(6-Fluorobenzo[d]thiazol-2-yl)phenyl)-1H-imidazol-5-yl)-2-methoxy benzenamine (4j);

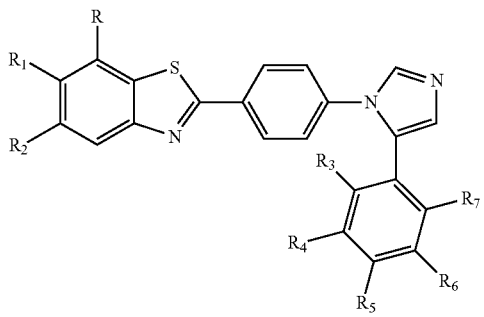

25 a-l

25a R$_3$ = R$_4$ = R$_6$ = R$_7$ = H; R$_6$ = NO$_2$; R = R$_2$ = H; R$_1$ = F
25b: R$_4$ = R$_6$ = R$_7$ = H; R$_3$ = NO$_2$; R$_5$ = OCH$_3$; R = R$_2$ = H; R$_1$ = F
25c: R$_3$ = R$_6$ = R$_7$ = H; R$_4$ = NO$_2$; R$_5$ = OCH$_3$; R = R$_2$ = H; R$_1$ = F
25d: R$_3$ = R$_4$ = R$_6$ = R$_7$ = H; R$_5$ = NO$_2$; R = R$_2$ = H; R$_1$ = OCH$_3$
25e: R$_4$ = R$_6$ = R$_7$ = H; R$_3$ = NO$_2$; R$_5$ = OCH$_3$; R = R$_2$ = H; R$_1$ = OCH$_3$
25f: R$_3$ = R$_6$ = R$_7$ = H; R$_4$ = NO$_2$; R$_5$ = OCH$_3$; R = R$_2$ = H; R$_1$ = OCH3
25g: R$_3$ = R$_4$ = R$_6$ = R7 = H; R$_5$ = NO$_2$; R = R$_2$ = OCH$_3$; R$_1$ = H
25h: R$_4$ = R$_6$ = R$_7$ = H; R$_3$ = NO$_2$; R$_5$ = OCH$_3$; R = R$_2$ = OCH$_3$; R$_1$ = H$_3$
25i: R$_3$ = R$_6$ = R$_7$ = H; R$_4$ = NO$_2$; R$_5$ = OCH$_3$; R = R$_2$ = OCH$_3$; R$_1$ = H
25j: R$_3$ = R$_4$ = R$_6$ = R$_7$ = H; R$_5$ = NO$_2$; R = R1 = R$_2$ = OCH$_3$;
25k: R$_4$ = R$_6$ = R$_7$ = H; R$_3$ = NO$_2$; R$_5$ = OCH$_3$; R = R$_1$ = R$_2$ = OCH$_3$;
25l: R$_3$ = R$_6$ = R$_7$ = H; R$_4$ = NO$_2$; R$_5$ = OCH$_3$; R = R$_1$ = R$_2$ = OCH$_3$;

vi. purifying the compound of formula 4a-g to 7a-g and 8a-b to 15a-b as obtained in step (v) and 4h-j to 7h-j as obtained in step (vi) by column chromatography using a solvent to obtain final compounds of formula A.

17. A process as claimed in step (v) of claim 16, wherein the substituted aldehyde used is selected from the group consisting of 22a-j, 23a-b and 24a-b

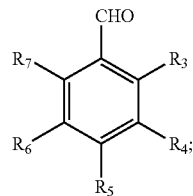

22a-j

22a: R$_3$ = R$_4$ = R$_5$ = R$_6$ = R$_7$ = H;
22b: R$_3$ = R$_4$ = R$_5$ = R$_6$ = R$_7$ = H; R$_5$ = CF$_3$
22c: R$_3$ = R$_6$ = R$_7$ = H; R$_4$ = OCH$_3$ R$_5$ = F
22d: R$_3$ = R$_5$ = R$_7$ = H; R$_4$ = R$_6$ = OCH$_3$
22e: R$_3$ = R$_6$ = R$_7$ = H; R$_4$ = R$_5$ = OCH$_3$
22f: R$_3$ = R$_7$ = H; R$_4$ = R$_5$ = R$_6$ = OCH$_3$
22g: R$_4$ = R$_6$ = H; R$_3$ = R$_5$ = R$_7$ = OCH$_3$
22h: R$_3$ = R$_4$ = R$_6$ = R$_7$ = H; R$_5$ = NO$_2$
22i: R$_4$ = R$_6$ = R$_7$ = H; R$_3$ = NO$_2$; R$_2$ = OCH$_3$
22j: R$_3$ = R$_6$ = R$_7$ = H; R$_4$ = NO$_2$; R$_5$ = OCH$_3$

23a-b

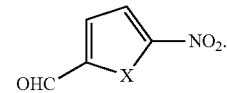

24a-b

X = NH, S

23a: R$_8$ = H;
23b: R$_8$ = OCH$_3$
24a: X = NH;
24b: X = S

18. A process as claimed in step (vii) of claim 16, wherein the solvent used is selected from the group consisting of ethyl acetate, hexane, chloroform and methanol.

\* \* \* \* \*